US009945811B2

United States Patent
Dressick et al.

(10) Patent No.: US 9,945,811 B2
(45) Date of Patent: Apr. 17, 2018

(54) ELECTROCHEMICAL PROBE FOR DETECTION OF CHLORATE EXPLOSIVES

(71) Applicant: The Government of the United States of America, as represented by the Secretary of the Navy, Washington, DC (US)

(72) Inventors: Walter J. Dressick, Waldorf, MD (US); Scott A. Trammell, Springfield, VA (US); Lisa C. Shriver-Lake, Gaithersburg, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 61 days.

(21) Appl. No.: 15/234,600

(22) Filed: Aug. 11, 2016

(65) Prior Publication Data

US 2018/0045678 A1 Feb. 15, 2018

(51) Int. Cl.
  *G01N 27/30* (2006.01)
  *G01N 27/48* (2006.01)
(52) U.S. Cl.
  CPC ............. *G01N 27/48* (2013.01); *G01N 27/30* (2013.01)
(58) Field of Classification Search
  CPC ...................................................... G01N 27/30
  See application file for complete search history.

(56) References Cited

U.S. PATENT DOCUMENTS

| 5,382,481 | A | * | 1/1995 | Fleischer | ............... | H01G 9/025 |
|  |  |  |  |  |  | 429/213 |
| 8,372,262 | B2 |  | 2/2013 | Foster |  |  |
| 2008/0182334 | A1 |  | 7/2008 | Amisar |  |  |
| 2014/0196180 | A1 |  | 7/2014 | Van Der Boom et al. |  |  |
| 2015/0226722 | A1 |  | 8/2015 | Sengupta et al. |  |  |
| 2015/0316523 | A1 |  | 11/2015 | Patolsky et al. |  |  |
| 2016/0061775 | A1 |  | 3/2016 | Zabetakis et al. |  |  |

OTHER PUBLICATIONS

International Search and Written Opinion dated Oct. 30, 2017 in PCT/2017/045836.
Cao et al., Electrochimica Acta 106 (2013) 465-471.
Fernandes, D. M.; Teixeira, A.; Freire, C. Langmuir 2015, 31, 1855-1865.
Itaya et al., J. Am. Chem. Sot. 1984, 106, 3423-3429.

* cited by examiner

*Primary Examiner* — Susan D Leong
(74) *Attorney, Agent, or Firm* — US Naval Research Laboratory; Roy Roberts

(57) ABSTRACT

A method of detecting chlorate in soil includes contacting soil wetted with a solvent containing an electrically conductive salt with an electrode comprising layers of vanadium-substituted phosphomolybdate alternating with layers of para-rosaniline, and performing voltammetry with the electrode, wherein a catalytic reduction current indicates a likelihood of the presence or absence of chlorate in the soil. A system includes a potentiostat operably connected to the electrode and in communication with hardware and software sufficient to produce an output indicating a chlorate level in soil.

12 Claims, 7 Drawing Sheets

ELECTROCHEMICAL PROBE FOR DETECTION OF CHLORATE EXPLOSIVES

CROSS-REFERENCE TO RELATED APPLICATIONS

This application is related to commonly-owned US Patent Application Publication 2016/0061775.

BACKGROUND

The manufacture and use of improvised explosive devices (IEDs) presents a serious hazard to military and civilian personnel in conflict zones throughout the world. Consequently, it is critically important to be able to identify and dismantle manufacturing sites for these devices before they can be fabricated and deployed. A key element in this strategy is the detection of the presence of residual explosive components at or near the sites, providing confirmation of illicit activity and allowing authorities to coordinate efforts to identify and detain persons associated with IED manufacture. As current detection methods for readily available nitrogen-based explosives continue to evolve in terms of sensitivity and selectivity,[1-5] however, enemy combatants are increasingly turning to alternate explosives based on chlorate or peroxides, for which fewer means of reliable detection in the field are available.

In particular, chlorate detection is complicated by a complex pH-dependent redox chemistry that facilitates (inter) conversion of chlorate to other chlorine-containing species such as hypochlorite, chlorite, chlorine dioxide, chlorine, and chloride.[6-8] Ion exchange chromatography provides a means for rapid separation of such Cl-containing species and, coupled with sensitive mass spectrometric detection, permits quantitative determination of each species in a laboratory setting.[9,10] However, carrying out such an analysis in the field, where rapid determinations must be made under often adverse conditions, presents serious logistical issues, especially in terms of safety, weight, and power requirements.

Simpler spectrophotometric methods for chlorate detection are, in theory, amenable for field use. These methods are generally based on bleaching of the color of a dye species[6,11-14] or the catalyzed generation of colored triiodide anion[15-18] in the presence of chlorate. The color change may be visible to the naked eye or with the aid of very simple instrumentation, permitting development of a lightweight system that requires little or no power to operate. However, specificity for chlorate detection generally remains an issue, since various other chlorine species such as hypochlorite, chlorite, chlorine, and chlorine dioxide are also strong oxidants capable of interfering and rendering a false positive signal.

Electrochemical methods that exploit the redox behavior of the chlorate species provide a convenient alternative to spectrophotometric detection methods. While electrochemical methods do require a power source, recent advances in electronics miniaturization and design can now provide lightweight, low-cost, rugged, low power potentiostats[19] that limit the impact of this issue. Because a simpler "yes or no" determination, rather than a quantitative chlorate analysis, may be sufficient for on-site testing in the field, any sensitivity issues related to the use of these simpler instruments are less of a concern. There are, however, several other issues associated with electrochemical detection of chlorate that must be addressed, especially for field work.

First among these is electrode type. Previous systems for analysis of chlorate were based primarily upon polarographic and related techniques using Hg electrodes,[20-25] which are not ideal for field use. During the 1990s, however, Gao and coworkers[26-30] extended earlier work by Unoura[31] and others[32,33] demonstrating catalytic electroreduction of chlorate by polyoxometalates and related transition metal compounds in solution at Pt and glassy carbon electrodes by developing electrocatalytic carbon paste electrodes impregnated with carboxylate ligand species and polyoxometalates as chlorate sensors. More recently, Jakmunee and coworkers[34] demonstrated amperometric detection of chlorate using a triiodide based scheme with stopped-flow injection, which was subsequently used for successful detection of chlorate in soil samples.[35]

A second issue is the potential interference due to electrochemical signatures of other chlorine-containing species, such as hypochlorite, chlorite, and chlorine dioxide, which may be present with chlorate or generated from it during the course of sampling and analysis. Significant efforts and progress have been made to address this concern. For example, rather than detect chlorate directly, Wen and coworkers[36] utilize it to selectively oxidize chalcopyrite (i.e., $CuFeS_2$) and electrochemically detect the Cu(II) and Fe(III) released. Similar strategies have been demonstrated using sphalerite (i.e., $ZnS_2$, producing Zn(II))[37] and galena (i.e., PbS, producing Pb(II))[38] as the metal ion sources. Elimination of Cl-containing interferences can also be accomplished via their preferential removal from a sample by reaction with $N_2H_5^+/OsO_4$,[39] $BH_4^-$,[40] or Fe(II)[6] and/or careful adjustment of the reaction conditions[41,42] prior to initiating the electrochemical analysis of chlorate. Finally, recent work indicates that selective surface modification of the electrode with rare earth coatings[43,44] can hinder the reduction of certain Cl-containing species, such as hypochlorite, in the presence of chlorate.

Despite these advancements, the electrochemical analysis of chlorate under ambient conditions in the field remains hindered by the presence of oxygen, whose reduction ($E_{pc}$>−0.3 V. vs. Ag/AgCl) is sufficiently close to that of chlorate ($E_{pc}$≈−0.4 V. vs. Ag/AgCl) to interfere with the analysis. Although the pH dependence of the oxygen reduction potential can be exploited to lessen this effect, it cannot be entirely removed. In similar fashion, any attempt to deconvolute measured current data to account for the oxygen contribution requires simultaneous measurement of the oxygen level and introduces additional complexity and error sources into the analysis. Removal of oxygen from the sample by purging with inert gas can certainly solve the problem, but at the expense of longer analysis times and added inert gas container weight, both of which are problematic for field use.

G. Cao et al.[45] described a technique wherein sulfur-polyoxometalate (POM) is mixed with methylene blue dye into a carbon paste, which is cast as an electrode. In the presence of 1M $H_2SO_4$ (strongly acidic conditions), this electrode could detect chlorate, however the electrode also exhibited significant instability. It is not apparent that this electrode could operate under, non-acidified conditions nor does not seem as if the electrode would have usefully long life in the field, and it must regularly by "renewed" by squeezing out fresh carbon paste containing the POM.

A need exists for an electrode that senses chlorate directly under ambient conditions from real world samples, such as soil, that may also be contaminated with traces of other electroactive species, such as humates, metal ions, and nitrogen-based explosives, among others.

BRIEF SUMMARY

One embodiment is a method of detecting chlorate in soil includes contacting soil wetted with a solvent containing an electrically conductive salt with an electrode comprising layers of vanadium-substituted phosphomolybdate alternating with layers of para-rosaniline, and performing voltammetry with the electrode, wherein a catalytic reduction current indicates a likelihood of the presence or absence of chlorate in the soil. This can be accomplished without excluding or removing oxygen from the testing environment and furthermore without the use of strong acid.

Another embodiment is a system for conducting the method, including a potentiostat operably connected to an electrode comprising layers of vanadium-substituted phosphomolybdate alternating with layers of para-rosaniline, and computer hardware and software in communication with the potentiostat and configured to produce an output indicating a chlorate level in soil in contact with the electrode.

DETAILED DESCRIPTION

Definitions

Figure 1A:
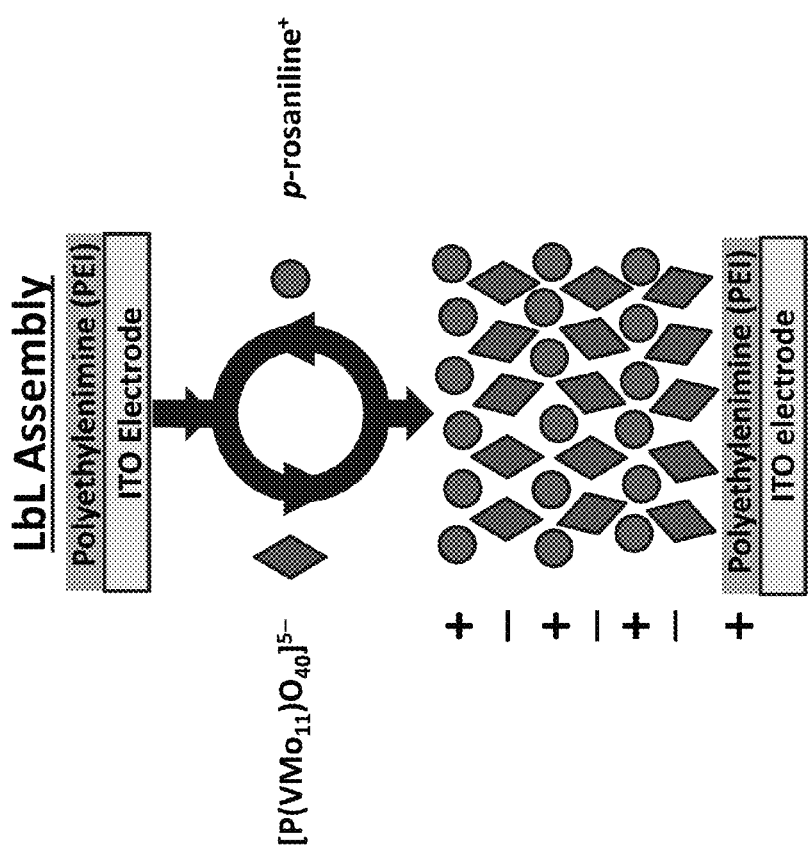
FIG. 1A is a schematic illustration of layer by layer (LbL) alternate electrostatic deposition of the Keggin-type polyoxometalate anion, $[PMo_{11}VO_{40}]^{5-}$ ($PMo_{11}V$), and the cationic dye, p-rosaniline acetate (PR) on indium tin oxide (ITO).

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Reference herein to the "likelihood of the presence or absence of chlorate" includes, unless the content clearly dictates otherwise, either or both a numerical representation of an expected chlorate concentration (in the desired units, for example molarity) or more simply a binary "yes/no" output indicating the likely presence or absence of chlorate

Overview

Described herein is a technique for the detection of chlorates, particularly chlorate explosives, that is operable in the presence of oxygen and not influenced by residual contaminants such as trinitrotoluene (TNT) or nitrates. The electrode exhibited good stability and resistance to degradation, with electrodes usable for a minimum of several months. The associated apparatus is light weight and provides a signal rapidly, on the order of two to five minutes.

A composite electrode operates to electrochemically detect the presence of chlorate explosive extracted from soil and other solid samples in solvent (e.g., water). The electrode comprises alternating layers of a vanadium-substituted phosphomolybdate polyoxometalate species and the dye, para-rosaniline. The invention allows detection of chlorate in soil samples obtained either directly by personnel or remotely via UAV to determine whether an area contains improvised explosive devices (IEDs) or a building or other structure is being used as a manufacturing site for IEDs. Chlorate is detected by its catalyzed electroreduction to chloride in and on the composite electrode.

The present inventors tested the ability of vanadium-substituted phosphomolybdate polyoxometalate/para-rosaniline electrodes[46] to efficiently reduce chlorate. In particular, the electrodes were composite, porous electrodes prepared via layer by layer (LbL) alternate electrostatic deposition of the Keggin-type polyoxometalate anion, $[PMo_{11}VO_{40}]^{5-}$ ($PMo_{11}V$), and the cationic dye, p-rosaniline acetate (PR). Electrocatalytic waves for the reduction of chlorate were observed using these electrodes under ambient conditions with no interference from oxygen. Described herein the preparation and characterization of an electrode system with respect to the factors electrode film age (A), solution acidity/pH (H), cyclic voltammetry (CV) scan speed (S), chlorate concentration (C), and number of $PMo_{11}V/PR$ bilayers (L) present in the electrode film. Electrode performance is optimized using a Taguchi L16 array and a two-level full factorial design provides a model predicting current for the detection of chlorate as a function of these parameters.

The examples use para-rosaniline/vanadium-substituted phosphomolybdate composite films in which the outermost film layer is para-rosaniline. Films in which the outermost layer is the vanadium-substituted phosphomolybdate should also have catalytic activity for chlorate electroreduction and detection, and thus are expected to operate similarly.

EXAMPLES

Materials—

Deionized water of 18.2 $M\Omega \cdot cm^{-1}$ resistivity obtained from a Milli-Q Advantage deionized water system was use to prepare all solutions and for all experiments. Filtered $N_2$ gas from liquid $N_2$ boil-off was used for drying samples during film deposition. All chemicals were used as received except where otherwise noted. Branched polyethylenimine (PEI; 50% wt. solution in water; $M_n$=60,000; $M_w$=750,000; [9002-98-6]), para-rosaniline acetate (PR; 90% dye; 347.41 $g \cdot mole^{-1}$; [6035-94-5]; $\varepsilon_{540\ nm}$=6.19×10$^4$ $L \cdot mole^{-1} \cdot cm^{-1}$; Caution—cancer suspect agent), vanadium (IV) oxide sulfate tetrahydrate ($VOSO_4 \cdot 4H_2O$; 97%; 235.04 $g \cdot mole^{-1}$; [123334-20-3]), sodium dihydrogen phosphate ($NaH_2PO_4$; ≥99.99%; 119.98 $g \cdot mole^{-1}$; [7558-80-7]), sodium acetate (NaOAc; ≥99.0%; 82.03 $g \cdot mole^{-1}$; [127-09-3]), potassium chlorate ($KClO_3$; ≥99.0%; 122.55 $g \cdot mole^{-1}$; [3811-04-9]; Caution—strong oxidizer), glacial acetic acid (HOAc; ≥99.7%; 60.05 $g \cdot mole^{-1}$; $\rho$=1.049 $g \cdot mL^{-1}$; [64-19-7]), methanol ($CH_3OH$; ≥99.0%; 32.04 $g \cdot mole^{-1}$; [67-56-1]), and sodium chloride (NaCl; ≥99.99%; 58.44 $g \cdot mole^{-1}$; [7647-14-5]) were all from Sigma-Aldrich Chemicals. N-(2-aminoethyl)-3-aminopropyltrimethoxysilane (EDA; 95% technical grade; 226.36 $g \cdot mole^{-1}$; $\rho$=1.019 $g \cdot mL^{-1}$; [1760-24-3]) from Gelest Inc. was vacuum distilled (140° C., 15 mm Hg) immediately prior to use. Sodium molybdate dihydrate ($Na_2MoO_4 \cdot 2H_2O$; 99%; 241.95 $g \cdot mole^{-1}$; [10102-40-6]) was obtained from Strem Chemicals. Concentrated hydrochloric acid (HCl; 36.46 $g \cdot mole^{-1}$; [7647-01-0]) and sulfuric acid ($H_2SO_4$; 98.18 $g \cdot mole^{-1}$; [7664-93-9]) were both ACS Reagent Grade from Fisher Scientific. Quartz slides (50 mm×25 mm×1 mm) were purchased from Dell Optics, Orange, N.J. and indium tin oxide (ITO) slides (part no. CB-50IN-S111), each bearing an ITO coating ($R_s$=5-15$\Omega$) on one side of a piece of Corning 1737F aluminosilicate glass (75 mm×25 mm×1.1 mm), were from Delta Technologies Limited, Stillwater, Minn.

$Na_4H[(VMo_{11})O_{40}]$ (i.e., $PMo_{11}V$; 1839.21 $g \cdot mole^{-1}$) was prepared at reduced scale with some modification of the literature method[47] as follows: A solution of 0.44 g $VOSO_4 \cdot 4H_2O$ in 9 mL 0.10 M HCl (aq) solution was freshly prepared. A second solution containing 0.054 g $NaH_2PO_4$ and 1.21 g $Na_2MoO_4 \cdot 2H_2O$ in 20 mL water was then prepared. The $VOSO_4$ solution was then added to the well stirred $NaH_2PO_4/Na_2MoO_4 \cdot 2H_2O$ solution. The stirred blue-black solution (characteristic of the $V^{IV}$ form of the product)[47] formed was titrated with 3.0 M HCl (aq) dropwise to pH 3.5 using a pH meter. After stirring at room temperature for 30 min, the blue-black solution was quickly frozen at −20° C. for 90 min in a freezer and transferred to a freeze dryer. After freeze drying 4 days the water had been removed, leaving 1.53 g of a gray-black solid that dissolves readily in water to form a dark blue solution that slowly (hours) becomes orange-brown in color. The gray-black solid was used immediately for film depositions, but can also be stored in the −20° C. freezer with no apparent change in color by eye for at least 4 months.

Solutions—

Stock PEI (~5 mg/mL) solution was freshly prepared just prior to use by weighing 1.0 g 50% wt. PEI (aq) solution into a tared 125 mL Ehrlenmeyer flask, adding sufficient water to bring the total solution weight to 100 g, and carefully stirring the mixture until the PEI had completely dissolved. A 0.10 M HOAc (aq) solution was prepared by pipetting 2.90 mL HOAc into a 500 mL volumetric flask containing 100 mL water and diluting to the mark with water. A 0.10 M NaOAc (aq) solution was prepared by quickly weighing 0.820 g anhydrous NaOAc into a 100 mL volumetric flask, adding ~30 mL water to dissolve the solid, and diluting to the mark with water. Stock pH ~4/0.10 M acetate buffer was prepared by pipetting 90.00 mL of the 0.10 M NaOAc (aq) solution into a 500 mL volumetric flask and diluting to the mark using the 0.10 M HOAc (aq) solution, yielding a solution having measured pH=3.99±0.02. Stock ~0.14 mM PR solution was prepared by weighing 5.3 mg of PR into a 100 mL volumetric flask and diluting to the mark with stock pH ~4/0.10 M acetate buffer. Stock $PMo_{11}V$ (2 mg/mL≅1.09 mM) solution was freshly prepared immediately prior to use by dissolving ~22 mg of $Na_4H[(VMo_{11})O_{40}]$ solid in 11 mL of the pH 4/0.10 M acetate buffer.

Chlorate-containing solutions for initial experiments were prepared by dissolving appropriate quantities of $KClO_3$ in a 100 mM sodium acetate solution whose pH had been adjusted to pH ~2.5 using hydrochloric acid. Chlorate-containing solutions having $\mu$=0.10 M total ionic strength for electrochemical studies related to the Taguchi and two-level full factorial statistically designed experiments were prepared from the following stock solutions: Solution A (0.095 M NaCl (aq)) was prepared by dissolving 1.388 g NaCl in water in a 250 mL volumetric flask and diluting to the mark with water. Solution B (0.100 M NaCl (aq)) was prepared by dissolving 5.844 g NaCl in water in a 1 L volumetric flask and diluting to the mark with water. Solution C (0.0625 M HCl (aq)/0.0375 M NaCl (aq)) was prepared by dissolving 1.096 g NaCl in ~100 mL water in a 500 mL volumetric flask, adding 2.60 mL concentrated HCl by pipet, and diluting to the mark with water. These stock solutions were prepared and stored until needed for experiments. Solution D (0.005 M $KClO_3$ ($KClO_3$ (aq)/0.095 M NaCl (aq)) was freshly prepared each day by weighing 61.3 mg $KClO_3$ into a 100 mL volumetric flask, dissolving the solid in 30 mL Solution A, and diluting to the mark with Solution A. Chlorate-containing solutions with specific pH and [$KClO_3$] values for electrochemical studies were prepared by mixing Solutions B, C, and D in the appropriate ratios. Corresponding blank solutions for the determination of background currents were prepared by replacing Solution D in each formulation by an equivalent volume of Solution B.

Instruments and Measurements—

Solution pH values were measured using a Corning Pinnacle 530 pH meter equipped with an AccuTupH+pH electrode (cat. no. 13-620-185). UV-visible spectra were measured using a double beam Varian Cary 5000 spectrophotometer. Spectra of $PMo_{11}V/PR$ films were corrected for baseline variations using EDA-coated quartz reference slides, prepared as described previously,[48] as blanks. Solution spectra were recorded vs. solvent blanks in matched 1.00 cm or 0.10 cm pathlength quartz cuvettes. A VirTis benchtop K freeze dryer was used to isolate solid $Na_4H[(VMo_{11})O_{40}]$ following its preparation (vide supra). All cyclic voltammetry (CV) measurements were performed using a three-electrode configuration with a model 440 electrochemical workstation (CH Instruments, Austin, Tex.) interfaced to a Gateway E-1200 personal computer for data acquisition and processing. The ITO working electrode coated by the $PMo_{11}V/PR$ film, Pt wire counter electrode, and Ag/AgCl reference electrode (Cypress Inc.) were used in a standard Teflon electrochemical quartz crystal microbalance (EQCM) cell (CH instruments, Austin, Tex., cat. no. CH1127) that was securely mounted and reproducibly positioned using a chuck on a Mellis-Griot optical bench as described in detail previously.[49] For the Taguchi and two-level full factorial design experiments, the Teflon cell was replaced by a rectangular Press-to-Seal Silicone Isolator gasket (Grace Bio-Labs, Inc., Bend, Oreg.; catalog no. 664116; 50 mm×25 mm×1 mm). The gasket contained an array of 10 isolated chamber holes 7 mm×7 mm×1 mm each) and formed a water-tight seal when clamped on the ITO electrode surface,[50] permitting up to 10 separate and independent current measurements per ITO electrode to be made. Each ITO/gasket well was used for an individual measurement of the chlorate blank, followed by the appropriate chlorate-containing solution to eliminate electrode cross contamination possibilities. Before the chlorate measurement, the multilayers with the corresponding pH solution were equilibrated by 4 successive CV sweeps from 0.8 V to −0.45 V vs. Ag/AgCl. Measured currents were corrected for background capacitive contributions at 0.7 V vs. Ag/AgCl where only non-faradaic processes were observed in the voltammograms. The net currents were averaged from three corrected CV scans using $E_{pc}$=−0.4 V vs. Ag/AgCl for the electrocatalytic chlorate reduction wave.

LbL Film Depositions—

Quartz slides were cleaned by successive 30 min immersions in 1:1 v/v $HCl/CH_3OH$ and concentrated $H_2SO_4$ with copious water rinsing after each treatment per the literature procedure.[48] For initial experiments, the ITO slides were cleaned by rinsing with water and soaking for 20 min in $H_2SO_4$, followed by copious rinsing with water. Because $H_2SO_4$ slowly removes ITO from the glass surface during the cleaning process, ITO substrates used for the Taguchi and two-level full factorial design experiments for optimization and modeling of electrode performance were cleaned in $H_2SO_4$ for only 10 min to maximize the current response and current response differences among the conditions tested. Cleaned quartz and ITO substrates were immediately coated with PEI film by immersion in the stock PEI solution for ~1 h, followed by triple rinsing with water and drying in a stream of filtered $N_2$ gas. PEI-coated substrates were stored in Parafilm™-sealed capped Coplin jars until needed for experiments. The PEI-coated quartz and ITO substrates were used within 1 week for film deposition.

For LbL deposition of the $PMo_{11}V/PR$ films, the PEI-coated quartz and ITO substrates were loaded onto a glass carousel, which was then immersed in the stock 2 mg/mL $PMo_{11}V$ solution (i.e., ~1.09 mM) for 10 min. The substrates were then triple rinsed in water and dried in the stream of filtered $N_2$ gas. Afterwards substrates were immersed in the stock 0.14 mM PR solution for 10 min, triple rinsed in water, and dried in the filtered $N_2$ gas stream. This sequence was repeated until films bearing the desired number of $PMo_{11}V/PR$ bilayers, "n", of structure Substrate/PEI/($PMo_{11}V$/PR). were deposited. FIG. 1A is a schematic illustration of this process. All films having n≤20 were deposited without interruption during a single day of work. The samples were stored in Parafilm™-sealed capped Coplin jars for up to 8 weeks until needed for experiments. UV-visible absorbance spectra of the films were periodically recorded as a function of the number of $PMo_{11}V$/PR bilayers deposited.

Statistically Designed Experiments—

The Taguchi design consisted of an L16 array that examined the importance of the L, H, C, S, and A variables in 16 total experiments, with each variable assessed at 4 levels to determine the conditions for optimum (i.e., maximum current) electrode response. A two-level full factorial design was subsequently employed for the analysis of the effects of the L, H, C, and S variables for electrodes aged A=8 weeks to provide a quantitative model relating current response to the levels of these variables. For each design, experiments were performed in random order to minimize the effects of cumulative error. While the two-level factorial design experiments were completed in ~6 h during a single day, the Taguchi design required 8 weeks in order to assess the effect of the film age variable, A. During this time the laboratory temperature was maintained at 22±1° C. with relative humidity at 45±5% and the film-coated electrodes were sealed in Coplin jars to control environmental effects that could introduce additional error into the measurements. Current measurements obtained for the Taguchi design were analyzed by the mean statistical analysis approach[51] to determine the effects of each variable. Corresponding statistically significant effects and residuals for the two-level full factorial design were determined using the Yates' Algorithm and Reverse Yates' Algorithm, respectively, leading directly to a predictive model of the dependence of the electrode current on the statistically significant L, H, C, and S variables and interactions.[52]

Results—

The preparation of bilayer films from $PMo_{11}V$ and PR via the LbL approach on quartz slides and glassy carbon electrodes (GCE) coated by PEI was originally described by Fernandes, et. al.[46] They demonstrated monotonic (i.e., nearly linear) film growth as a function of number of bilayers, with overnight interruptions of the deposition process leading to variations in the subsequent growth rate consistent with reorganization of internal structure during film aging. Thicknesses as large as ~150 nm were observed for films containing 20 bilayers, with measured roughnesses of ~64 nm. Film morphology characteristic of a globular, rather than stratified structure, was also noted consistent with roughness results and electrochemical measurements indicating permeability of the films to ferrocyanide redox probe anions. Reversible one-electron waves in the film CV due to $V^{IV/V}$ at $E_{pc}$=0.367 V and $Mo^{VI/V}$ at 0.098 V, −0.122 V, and −0.266 V vs. Ag/AgCl further confirmed redox activity and accessibility of solution species to the $PMo_{11}V$ component. Film growth was rather insensitive to [$PMo_{11}V$] in the 1.0 mM [$PMo_{11}V$]≤5.0 mM range for n<8 bilayers, though somewhat thinner films were observed using the higher [$PMo_{11}V$] in this range when films having n 8 bilayers were examined. However, deposition times more strongly influenced film growth, with 10 min treatment times using the $PMo_{11}V$ and PR solutions providing thicker films than 5 min or 20 min treatments.

Figure 1C:
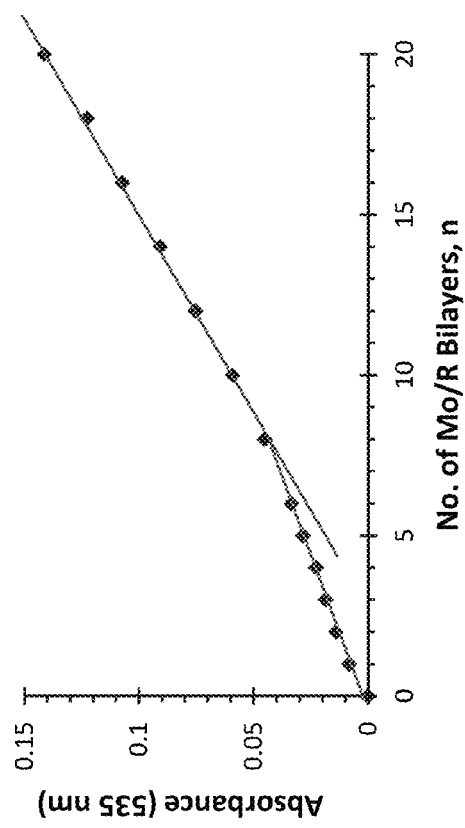
FIG. 1C shows para-rosaniline absorbance at 535 nm vs. number of $PVMo_{11}/PR$ bilayers deposited. Two linear fits of the data are shown. The data from n=0-6 obey the equation: $A=0.0053n+0.002$, $r^2=0.9907$. The data from n=6-20 obey the equation: $A=0.0078n-0.0164$, $r^2=0.9973$.
Figure 1B:
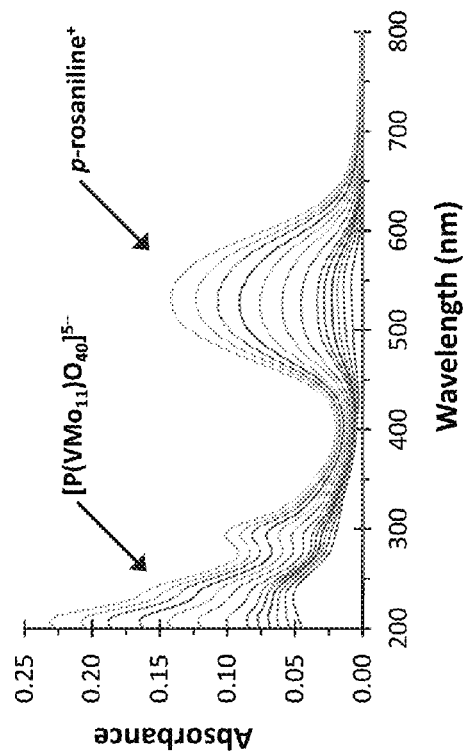
FIG. 1B shows absorbance spectra as a function of number of deposited $PVMo_{11}/PR$ bilayers. Spectra in order of increasing absorbance at 535 nm are shown for 1, 2, 3, 4, 5, 6, 8, 10, 12, 14, 16, 18, and 20 bilayers.

Given these favorable characteristics, $PMo_{11}V$/PR films were fabricated on PEI-coated quartz and ITO slides for chlorate electrocatalysis studies using 2 mg/mL (i.e., 1.09 mM) $PMo_{11}V$ and ~0.14 mM PR solutions in pH ~4 0.10 M acetate buffer with 10 min substrate treatment times corresponding approximately to the optimum deposition conditions identified by Fernandes, et. al.[46] The films exhibited broadened absorbance spectra consistent with previous reports[46] in FIG. 1B for films on quartz as functions of the number of $PMo_{11}V/PR$ bilayers, n, for n=1-20. However, absorbance changes exhibited two linear regions with increasing numbers of $PMo_{11}V/PR$ bilayers, rather than a single nearly linear growth behavior, as shown in the FIG. 1C. In addition, the ~535 nm absorbance of the Quartz/PEI/ $(PMo_{11}V/PR)_{20}$ film was ~0.38, which is somewhat smaller than the ~0.46 value found for the corresponding film in the literature.[46]

In order to better understand the nature of these differences, the potential effects of the PEI layer on film deposition were examined. Films of structure Quartz/PEI/ $(PMo_{11}V/PR)_{20}$ were deposited on fresh PEI-coated quartz and PEI-coated quartz that had been stored in sealed Coplin jars for up to 1 week at room temperature. Absorbance values at 535 nm obtained for the films were 0.38 and 0.36, respectively, indicating that any changes in PEI conformation and degree of protonation or potential PEI reactions involving carbon dioxide[53] or other species present in the ambient atmosphere did not significantly affect film deposition.

Potential effects due to the preparation of the $Na_4H[(VMo_{11})O_{40}]$ (i.e., $PVMo_{11}$) species were examined. Films were prepared using $Na_4[(VMo_{11})O_{40}]$ that was freeze dried immediately after preparation, preserving the blue color corresponding to the $V^I$ form of the material in the resulting solid.[47] Dissolution of this material in pH 4/0.1 M acetate buffer (aq) resulted in a blue solution, which was immediately used to deposit the films. The solution color slowly changed to orange-brown, corresponding to the $V^V$ form of the material, with increasing time at room temperature. Completion of the color change corresponded approximately to the time required to deposit 5-7 $PMo_{11}V/PR$ bilayer, suggesting that the multi-slope behavior and breakpoint observed in FIG. 1C were related to the change in oxidation state of the $PMo_{11}V$ species. Because the $V^{IV}$ form of the $PMo_{11}V$ possesses an additional unit of negative charge compared to the $V^V$ form, differences in packing density with PR, film hydration, and inclusion of solution anions such as $OAc^-$ are expected to occur during film deposition. These factors in turn will affect film growth rate and absorbance by altering the amounts of $PMo_{11}V$ and PR deposited.

Chlorate Electrochemistry—

Figure 2A:
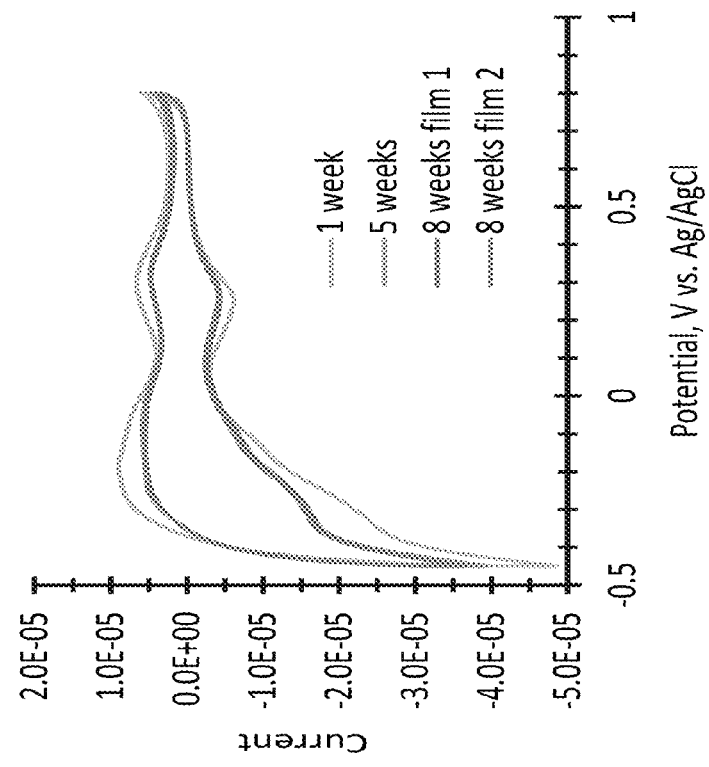
FIG. 2A shows cyclic voltammograms of $PVMo_{11}/PR$ bilayers (n=6) on ITO as a function scan rate. Cyclic voltammograms of $PVMo_{11}/PR$ bilayers (n=6) on ITO as a function scan rate.

FIG. 2A shows a series of cyclic voltammograms for a n=6 $PVMo_{11}/PR$ bilayer film on ITO in aerated 0.10 M sodium acetate pH 2.5 (aq) solution as a function of scan rate, together with a plot of the scan rate dependence of the current at $E_{pc}$=-0.250 V and $E_{pa}$=-0.203 V. Cathodic and anodic peak currents vary linearly with scan rate in FIG. 2B, as expected for surface confined processes.[54] The individual peaks observed in the -0.45≤E≤0.80 V potential range scanned are attributed to the polyoxometalate, with noticeable differences to the literature values[46] most likely do to different conditions e.g., ITO vs. GCE, pH ~2.5/0.10 M sodium acetate electrolyte vs. pH ~4/0.10 M sodium acetate (aq) buffer electrolyte, and PR-terminated vs. $PVMo_{11}$-terminated films, respectively.

TABLE 1

Electrochemical parameters for n = 6 $PVMo_{11}/PR$ bilayer film on ITO

| | This work[a] | | | Literature[b] | |
|---|---|---|---|---|---|
| Peak | $E_{pc}$ | $E_{pa}$ | $(\Delta E_p)$ | $E_{pc}$ | $(\Delta E_p)$ |
| 1 | 0.290 | 0.355[c] | 0.065 | 0.367 | 0.06 |
| 2a | 0.025 | 0.045 | 0.020 | 0.098 | 0.029-0.09 |
| 2b | -0.080 | -0.055 | 0.025 | — | — |
| 3 | -0.250 | -0.203 | 0.047 | -0.122 | 0.029-0.09 |
| 4 | -0.400 | -0.360 | 0.040 | -0.266 | 0.029-0.09 |

[a]Scan rate = 100 mV · s$^{-1}$
[b]Reference 46
[c]Shoulder at 0.53 V vs. Ag/AgCl The peak positions and assignments from the cyclic voltammograms are listed in Table 1. The cathodic peak potential ($E_{pc}$) of Peak 1 has shifted from $E_{pc}$=0.290 to 0.323 V compared to the literature. Peak 2 has split from a broad peak with $E_{pc}$=0.098 V to two peaks with $E_{pc}$=0.035 and -0.068 V. Peak 3 has shifted from $E_{pc}$=-0.122 to -0.250 V, and Peak 4 has shifted from $E_{pc}$=0.266 to $E_{pc}$=0.44 V. No redox processes are observed for the PR species. Peak-to-peak separations ($\Delta E_p$) of ~0.06 V are observed for the V-based wave assigned to Peak 1, whereas $\Delta E_p$ values between 0.02 to 0.05 V are noted for Mo-based waves assigned for Peaks 2 thru 4. Integration of the cathodic and anodic waves of Peak 1 yields a polyoxometalate surface coverage of $\Gamma$=0.16±0.05 nmole·cm$^{-2}$ for a film comprising n=6 bilayers.

Figure 3:
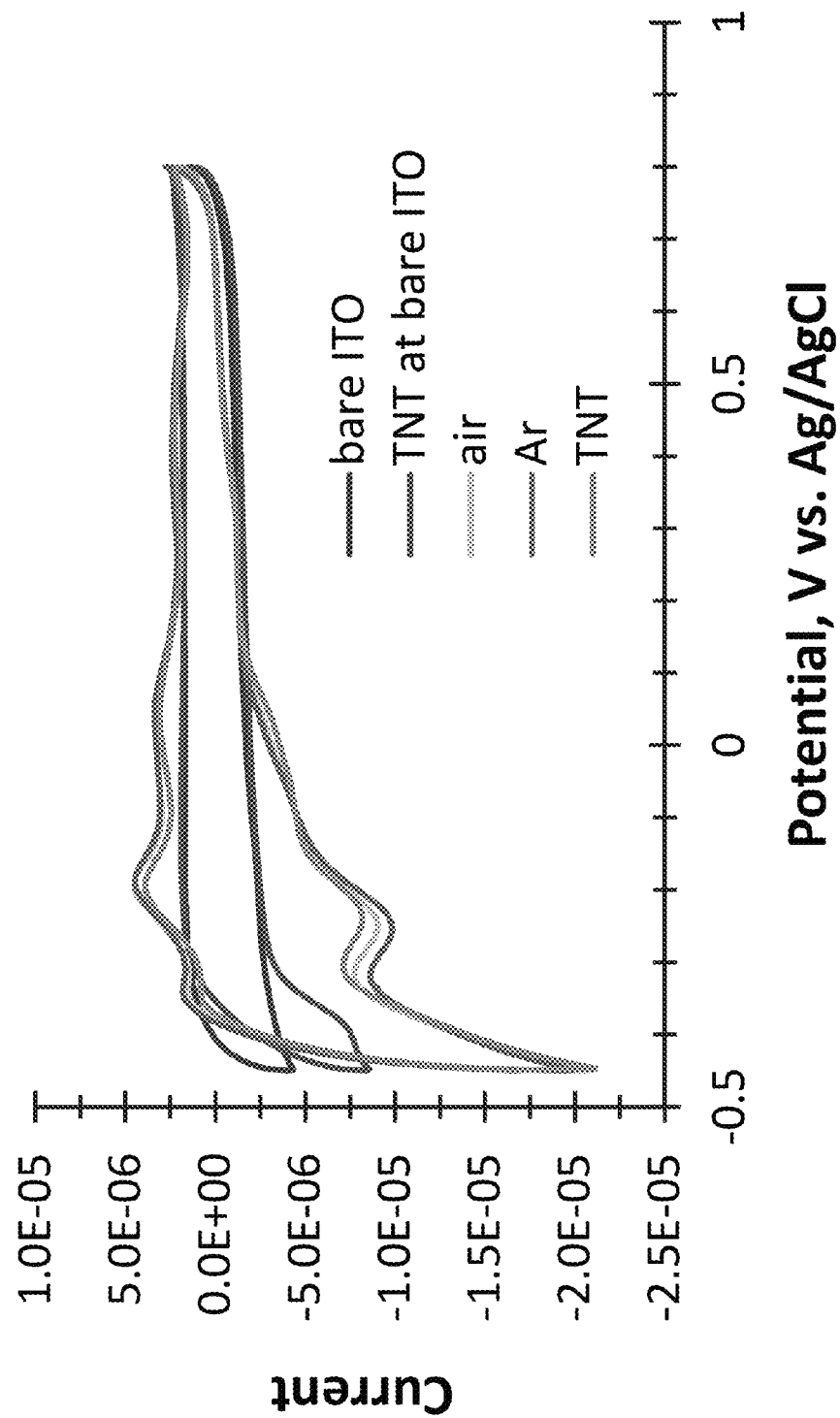
FIG. 3 shows cyclic voltammograms of ITO and $PVMo_{11}/PR$ bilayers (n=6) on ITO. Dark blue=bare ITO; Dark green=bare ITO+0.015 $mg \cdot mL^{-1}$ of TNT; Yellow=$PVMo_{11}/PR$ bilayers (n=6) on ITO in aerated solution; Light blue=$PVMo_{11}/PR$ bilayers (n=6) on ITO in solution purged with Ar; Light green=$PVMo_{11}/PR$ bilayers (n=6) on ITO+ 0.015 $mg \cdot mL^{-1}$ of TNT. Scan rate 50 $mV \cdot s^{-1}$. Electrolyte=100 mM sodium acetate at pH 2.5

FIG. 2A shows that redox processes associated only with the $PVMo_{11}$ component of the film are observed, even though the CV was carried out using aerated electrolyte solutions. This is further illustrated in FIG. 3, where essentially identical voltammograms are obtained for the composite electrode in aerated and Ar-purged buffer solutions. Likewise, the addition of TNT at trace levels (0.01 mg·mL$^{-1}$) to the solution provides no additional signals at the composite electrode in FIG. 3, consistent with the selective nature of the modified electrode.

Figure 2B:
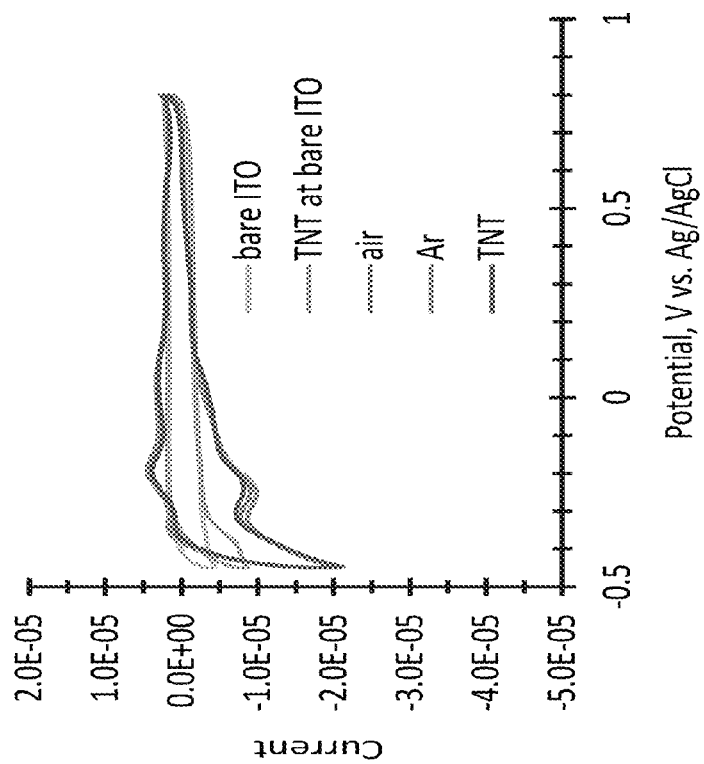
FIG. 2B shows cyclic voltammograms of ITO and $PVMo_{11}/PR$ bilayers (n=5) on ITO comparing different films aged at different times. Scan rate 50 $mV \cdot s^{-1}$. Electrolyte=100 mM sodium chloride adjusted to pH 2.86 with HCl. Yellow=1 week; Gray=5 weeks; Blue=8 weeks (film 1); Orange=8 weeks (film 2). Current measurements for the two films aged 8 weeks are identical within experimental error to the current obtained for the film aged 5 weeks, indicating that any changes in film structure are complete by 8 weeks and the films have reached equilibrium by that time. Identical currents within experimental error observed for the two 8 week old films demonstrate and confirm film deposition reproducibly.

Results of aging films and film deposition reproducibility can be seen in FIG. 2B, which shows cyclic voltammograms of ITO and $PVMo_{11}/PR$ bilayers (n=5) on ITO comparing different films aged at different times. Current measurements for the two films aged 8 weeks are identical within experimental error to the current obtained for the film aged 5 weeks, indicating that any changes in film structure are complete by 8 weeks and the films have reached equilibrium by that time. Identical currents within experimental error observed for the two 8 week old films demonstrate and confirm film deposition reproducibly.

Figures 4A, 4B:
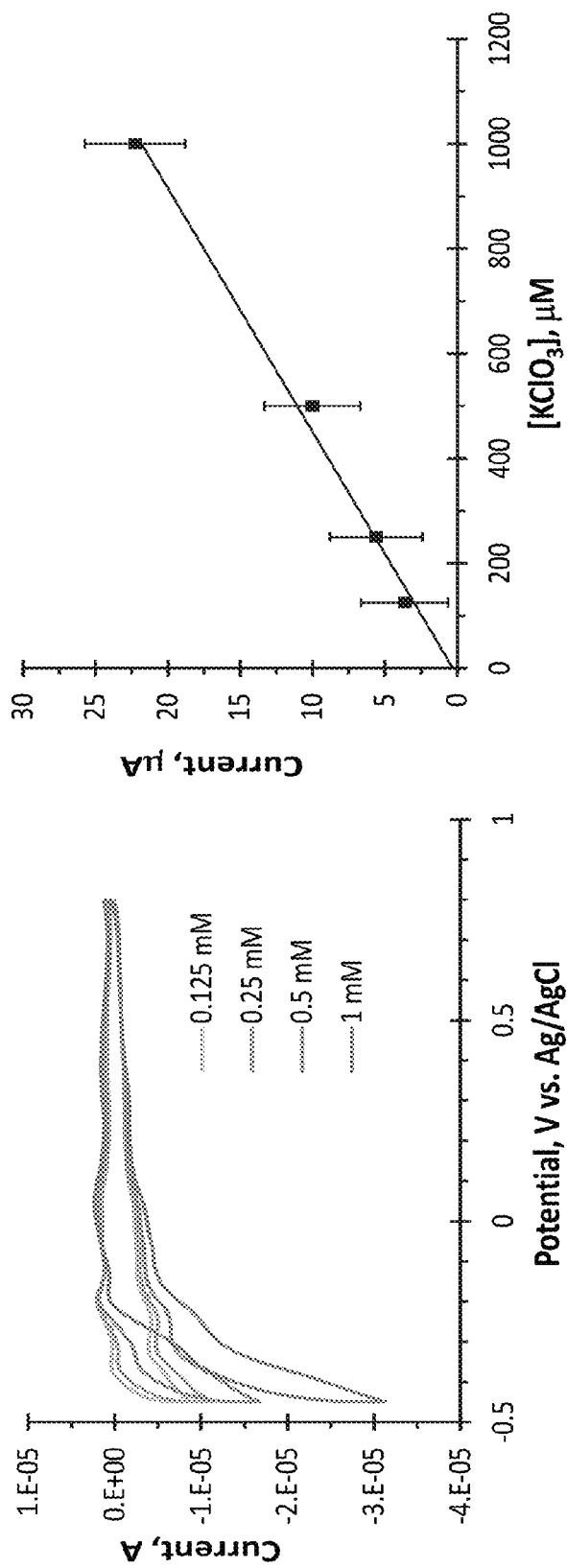
FIG. 4A shows cyclic voltammograms of $PVMo_{11}/PR$ bilayers on ITO with increasing $[KClO_3]$ concentration.
FIG. 4B. shows current ($\Delta i$) vs. $[KClO_3]$, µM (at −0.4 V. vs. Ag/AgCl) in aerated pH 2.5, 100 mM sodium acetate buffer. Scan rate=50 $mV \cdot s^{-1}$.

FIG. 4A illustrates the effect of the presence of chlorate in the solution on the CV of the 1 week old n=6 $PVMo_{11}/PR$ bilayer film on ITO. A strong catalytic wave is observed at the $E_{pc4}$ Mo-based wave, corresponding to the pH dependent catalyzed reduction of chlorate to chloride according to eq. (1) and (2):

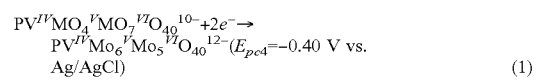

(1)

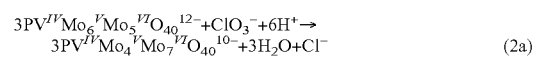

(2a)

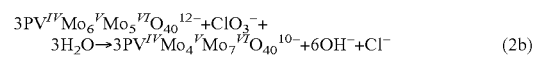

(2b)

Two one-electron reductions of Mo$^{VI}$ components of the $PVMo_{11}$ species in the film to the me oxidation state produce a highly reduced product in eq. (1) capable of reducing chlorate to chloride under acid or basic conditions in eqs. (2). The oxidized $PV^{IV}Mo_4{}^VMo_7{}^{VI}O_{40}{}^{10-}$ species produced as the product in eqs. (2) is identically the same species serving as reactant in eq. (1). At the applied electrode potential designated by $E_{pc4}$, it is immediately reduced once again to $PV^{IV}Mo_6{}^VMo_5{}^{VI}O_{40}{}^{12-}$ and reacts with additional chlorate to continue the catalytic cycle.

Catalytic reduction current increases with $[ClO_3{}^-]$ in solution in FIG. 4A, resulting in a linear calibration curve in FIG. 4B. The limit of detection (LOD) was calculated using the equation LOD=3σ/m where "σ" is the standard deviation of signal at the lowest concentration tested and "m" is the slope of the calibration curve. From FIG. 3B, the LOD=220 μM and the sensitivity=0.022±0.002 μA/μM of $KClO_3$. In small volume electrochemical cell of 100 μL, this would correspond to 2.6 μg of $KClO_3$, which is sufficient to provide a "yes/no" answer for detection of bulk chlorate salts in the field for surveillance of bomb making activities.

Electrode Performance Optimization—

Having completed the initial characterization of the electrodes and demonstrated their ability to catalyze electroreduction of chlorate, the next step was to determine conditions for optimum performance using a Taguchi L16 array. The factors (i.e., variables) examined included number of $PMo_{11}V$/PR bilayers present on the electrode (L), solution acidity/pH (H), solution $[ClO_3{}^-]$ (C; μM), CV scan rate (S; mV·s$^{-1}$), and $PMo_{11}V$/PR film age (A; weeks). Each factor was examined at k=4 levels at the following factor/level values as follows: L/1=3, L/2=4, L/3=5, and L/4=6 $PMo_{11}V$/PR bilayers; H/1=1.32±0.02, H/2=1.80±0.01, H/3=2.31±0.01, and H/4=2.85±0.03 pH units; C/1=250, C/2=500, C/3=750, and C4=1000 μM chlorate; S/1=50, S/2=100, S/3=150, and S/4=200 mV·s$^{-1}$ scan rate; A/1=1, A/2=2, A/3=5, and A/4=8 weeks aging.

Table 2 summarizes the Taguchi L16 array, with each row indicating an experiment at conditions corresponding to the coded values for each factor shown. Net currents obtained for each of x=3 replicates after subtraction of background currents and corrections for capacitive effects are shown, together with the average current and its standard deviation for each of m=16 total experiments. The S/N ratio is defined for optimization related to current maximization by summing the inverse squares of each net current measurement, dividing by the number of replicate measurements, "x=3", taking the base 10 logarithm of the value obtained, and finally multiplying that value by −10.

The mean S/N ratio of each factor, F, defined at each level, "i", of that factor is given by $M_i{}^F$. The $M_i{}^F$ are calculated by summing the four S/N values corresponding to a given fixed level for that factor and dividing by k=4 (i.e., the number of levels available for each factor). For example, factor A at level 2 (i.e., A/2) occurs in experiments 2, 7, 9, and 16, corresponding to S/N ratios of 23.54, 24.04, 37.51, and 36.86 in Table 2. These values are shown in the array in Table 3 as entries in columns j=1-4 in the A/2 row. Their sum is 121.96, which when divided by k=4 levels for each variable yields the $M_i{}^F=M_2{}^A=30.49$ value shown in Table 3 below. Population of the remaining $M_i{}^F$ in analogous fashion completes Table 3.

Conditions associated with the maximum current response for the electrode correspond to the levels of each factor having the largest $M_i{}^F$ value. In this case, the maximum current response corresponds to the L/3, H/4, C/4, S/4, A/1 factor level combination indicated in bold italic text in Table 3. That is, an electrode comprising L=5 bilayers aged A=1 week in a solution containing C=1000 μM chlorate at H=2.85 pH scanned at S=200 mV·s$^{-1}$ provides the largest current response.

TABLE 2

Taguchi L16 Array

| Expt. No. | Variables | | | | | Net Current, i (μA) | | | Average $i_{ave}$ (μA) | Standard Deviation (σ) | S/N Ratio |
|---|---|---|---|---|---|---|---|---|---|---|---|
| | L | H | C | S | A | $i_1$ | $i_2$ | $i_3$ | | | |
| 1 | 1 | 1 | 1 | 1 | 1 | 8.69 | 6.89 | 6.06 | 7.21 | 0.87 | 16.88 |
| 2 | 1 | 2 | 2 | 2 | 2 | 17.49 | 14.77 | 13.57 | 15.28 | 1.31 | 23.54 |
| 3 | 1 | 3 | 3 | 3 | 3 | 16.62 | 15.47 | 14.98 | 15.69 | 0.55 | 23.89 |
| 4 | 1 | 4 | 4 | 4 | 4 | 49.26 | 40.56 | 37.20 | 42.34 | 4.12 | 32.36 |
| 5 | 2 | 1 | 2 | 3 | 4 | 41.65 | 34.86 | 33.58 | 36.70 | 3.05 | 31.18 |
| 6 | 2 | 2 | 1 | 4 | 3 | 43.12 | 32.82 | 29.96 | 35.30 | 4.74 | 30.65 |
| 7 | 2 | 3 | 4 | 1 | 2 | 18.94 | 15.75 | 14.18 | 16.29 | 1.56 | 24.05 |
| 8 | 2 | 4 | 3 | 2 | 1 | 42.59 | 36.58 | 33.70 | 37.62 | 2.93 | 31.39 |
| 9 | 3 | 1 | 3 | 4 | 2 | 84.37 | 72.68 | 70.22 | 75.76 | 5.28 | 37.51 |
| 10 | 3 | 2 | 4 | 3 | 1 | 121.39 | 110.27 | 104.17 | 111.95 | 5.54 | 40.93 |
| 11 | 3 | 3 | 1 | 2 | 4 | 30.97 | 25.42 | 23.06 | 26.48 | 2.66 | 28.27 |
| 12 | 3 | 4 | 2 | 1 | 3 | 22.44 | 19.34 | 17.62 | 19.80 | 1.55 | 25.81 |
| 13 | 4 | 1 | 4 | 2 | 3 | 39.05 | 28.03 | 24.22 | 30.43 | 5.16 | 29.17 |
| 14 | 4 | 2 | 3 | 1 | 4 | 14.93 | 12.46 | 11.43 | 12.94 | 1.18 | 22.08 |
| 15 | 4 | 3 | 2 | 4 | 1 | 100.70 | 81.71 | 73.93 | 85.45 | 9.07 | 38.42 |
| 16 | 4 | 4 | 1 | 3 | 2 | 82.25 | 68.55 | 62.32 | 71.04 | 6.63 | 36.86 |

TABLE 3

Mean S/N Ratios for Each Factor

| Factor/ Level | $[(S/N)_i{}^F]_j$ | | | | | Experimental Conditions |
|---|---|---|---|---|---|---|
| | j = 1 | j = 2 | j = 3 | j = 4 | $M_i{}^F$ | |
| L/1 | 16.88 | 23.54 | 23.89 | 32.36 | 24.17 | L/1 = 3 bilayers |
| L/2 | 31.18 | 30.65 | 24.05 | 31.39 | 29.32 | L/2 = 4 bilayers |
| *L/3* | *37.51* | *40.93* | *28.27* | *25.81* | *33.13* | *L/3=5 bilayers* |

TABLE 3-continued

Mean S/N Ratios for Each Factor

| Factor/ Level | $[(S/N)_i{}^F]_j$ | | | | | Experimental Conditions |
|---|---|---|---|---|---|---|
| | j = 1 | j = 2 | j = 3 | j = 4 | $M_i{}^F$ | |
| L/4 | 29.17 | 22.08 | 38.42 | 36.86 | 31.63 | L/4 = 6 bilayers |
| H/1 | 16.88 | 31.18 | 37.51 | 29.17 | 28.68 | H/1 = 1.32 ± 0.02 pH |

TABLE 3-continued

Mean S/N Ratios for Each Factor

| Factor/Level | $[(S/N)_i^F]_j$ | | | | $M_i^F$ | Experimental Conditions |
|---|---|---|---|---|---|---|
| | j = 1 | j = 2 | j = 3 | j = 4 | | |
| H/2 | 23.54 | 30.65 | 40.93 | 22.08 | 29.30 | H/2 = 1.80 ± 0.01 pH |
| H/3 | 23.89 | 24.05 | 28.27 | 38.42 | 28.66 | H/3 = 2.31 ± 0.01 pH |
| *H/4* | *32.36* | *31.39* | *25.81* | *36.86* | *31.60* | *H/4 = 2.85 ± 0.03 pH* |
| C/1 | 16.88 | 30.65 | 28.27 | 36.86 | 28.17 | C/1 = 250 μM $ClO_3^-$ |
| C/2 | 23.54 | 31.18 | 25.81 | 38.42 | 29.74 | C/2 = 500 μM $ClO_3^-$ |
| C/3 | 23.89 | 31.39 | 37.51 | 22.08 | 28.72 | C/3 = 750 μM $ClO_3^-$ |
| *C/4* | *32.36* | *24.05* | *40.93* | *29.17* | *31.63* | *C/4 = 1000 μM $ClO_3^-$* |
| S/1 | 16.88 | 24.05 | 25.81 | 22.08 | 22.20 | S/1 = 50 mV · s$^{-1}$ |
| S/2 | 23.54 | 31.39 | 28.27 | 29.17 | 28.09 | S/2 = 100 mV · s$^{-1}$ |
| S/3 | 23.89 | 31.18 | 40.93 | 36.86 | 33.21 | S/3 = 150 mV · s$^{-1}$ |
| *S/4* | *32.36* | *30.65* | *37.51* | *38.42* | *34.74* | *S/4 = 200 mV s$^{-1}$* |
| *A/1* | *16.88* | *31.39* | *40.93* | *38.42* | *31.90* | *A/1 = 1 week aged* |
| A/2 | 23.54 | 24.05 | 37.51 | 36.86 | 30.49 | A/2 = 2 weeks aged |
| A/3 | 23.89 | 30.65 | 25.81 | 29.17 | 27.38 | A/3 = 5 weeks aged |
| A/4 | 32.36 | 31.18 | 28.27 | 22.08 | 28.47 | A/4 = 8 weeks aged |

From the Taguchi analysis, the relative contributions and influences of the L, H, C, S, and A factors on system performance were estimated via a standard ANOVA calculation. The percentage contribution of each factor, F, at level "i", $R_i^F$, is first calculated. The calculation is identical to that performed for the $M_i^F$ of Table 3, with the exception that Ave. Current Results, rather than individual S/N, from Table 2 are used in the calculation. The results are shown in Table 4 below.

TABLE 4

$R_i^F$ Calculations

| Factor/Level | $[(R_A)_i^F]_j$ | | | | $R_i^F$ |
|---|---|---|---|---|---|
| | j = 1 | j = 2 | j = 3 | j = 4 | |
| L/1 | 7.21443 | 15.2766 | 15.6903 | 42.3397 | 20.1303 |
| L/2 | 36.7 | 35.3004 | 16.2874 | 37.6199 | 31.4769 |
| L/3 | 75.7572 | 111.947 | 26.4814 | 19.8011 | 58.4967 |
| L/4 | 30.4321 | 12.9367 | 85.4472 | 71.0404 | 49.9641 |
| H/1 | 7.21443 | 36.7 | 75.7572 | 30.4321 | 37.5259 |
| H/2 | 15.2766 | 35.3004 | 111.947 | 12.9367 | 43.8652 |
| H/3 | 15.6903 | 16.2874 | 26.4814 | 85.4472 | 35.9766 |
| H/4 | 42.3397 | 37.6199 | 19.8011 | 71.0404 | 42.7003 |
| C/1 | 7.21443 | 35.3004 | 26.4814 | 71.0404 | 35.0092 |
| C/2 | 15.2766 | 36.7 | 19.8011 | 85.4472 | 39.3062 |
| C/3 | 15.6903 | 37.6199 | 75.7572 | 12.9367 | 35.501 |
| C/4 | 42.3397 | 16.2874 | 111.947 | 30.4321 | 50.2515 |
| S/1 | 7.21443 | 16.2874 | 19.8011 | 12.9367 | 14.0599 |
| S/2 | 15.2766 | 37.6199 | 26.4814 | 30.4321 | 27.4525 |
| S/3 | 15.6903 | 36.7 | 111.947 | 71.0404 | 58.8444 |
| S/4 | 42.3397 | 35.3004 | 75.7572 | 85.4472 | 59.7111 |
| A/1 | 7.21443 | 37.6199 | 111.947 | 85.4472 | 60.5571 |
| A/2 | 15.2766 | 16.2874 | 75.7572 | 71.0404 | 44.5904 |
| A/3 | 15.6903 | 35.3004 | 19.8011 | 30.4321 | 25.306 |
| A/4 | 42.3397 | 36.7 | 26.4814 | 12.9367 | 29.6144 |

TABLE 5

Summary of $SS_F$ Calculations

| Factor | $SS_F$ Values | | $DF_F$ Values | |
|---|---|---|---|---|
| L | $SS_L =$ | 10906.3 | $DF_L =$ | 3 |
| H | $SS_H =$ | 534.461 | $DF_H =$ | 3 |
| C | $SS_C =$ | 1808.68 | $DF_C =$ | 3 |
| S | $SS_S =$ | 18887.6 | $DF_S =$ | 3 |
| A | $SS_A =$ | 9209.26 | $DF_A =$ | 3 |

Completion of the ANOVA calculations required knowledge of the total sum of squares, $SS_T$. Table 6 below shows the squared results for each net current measurement shown in Table 2 used to calculate $SS_T$ via the following equation:

$$SS_T = \Sigma_{j=1}^m (\Sigma_{i=1}^x R_i^2)_j - (mx)R_T^2 = 42647.19984 \quad (6)$$

TABLE 6

Squares of the Net Currents

| Expt. No. | Factors | | | | | Squares of Net Currents | | |
|---|---|---|---|---|---|---|---|---|
| | L | H | C | S | A | $i_1^2$ | $i_2^2$ | $i_3^2$ |
| 1 | 1 | 1 | 1 | 1 | 1 | 75.5874 | 47.4804 | 36.7066 |
| 2 | 1 | 2 | 2 | 2 | 2 | 305.97 | 218.212 | 184.031 |
| 3 | 1 | 3 | 3 | 3 | 3 | 276.234 | 239.265 | 224.475 |
| 4 | 1 | 4 | 4 | 4 | 4 | 2426.45 | 1645.09 | 1383.86 |
| 5 | 2 | 1 | 2 | 3 | 4 | 1735.06 | 1215.37 | 1127.86 |
| 6 | 2 | 2 | 1 | 4 | 3 | 1859.16 | 1077.06 | 897.883 |
| 7 | 2 | 3 | 4 | 1 | 2 | 358.538 | 247.955 | 201.087 |
| 8 | 2 | 4 | 3 | 2 | 1 | 1813.6 | 1337.92 | 1135.39 |
| 9 | 3 | 1 | 3 | 4 | 2 | 7118.47 | 5281.74 | 4931.54 |
| 10 | 3 | 2 | 4 | 3 | 1 | 14736.3 | 12160.5 | 10852 |
| 11 | 3 | 3 | 1 | 2 | 4 | 958.85 | 646.202 | 531.694 |
| 12 | 3 | 4 | 2 | 1 | 3 | 503.558 | 374.07 | 310.549 |
| 13 | 4 | 1 | 4 | 2 | 3 | 1524.77 | 785.839 | 586.38 |
| 14 | 4 | 2 | 3 | 1 | 4 | 222.782 | 155.174 | 130.582 |
| 15 | 4 | 3 | 2 | 4 | 1 | 10140.7 | 6676.83 | 5465.47 |
| 16 | 4 | 4 | 1 | 3 | 2 | 6765.59 | 4699.01 | 3883.61 |

Using the $SS_T$ and $SS_F$ values, the sum of the squares of the experimental error, $SS_{ERROR}$, and the variance of the error, $V_{ERROR}$, were calculated from the following equations:

$$SS_{ERROR} = SS_T - \Sigma_{F=A}^F (SS_F) = 1300.907799 \quad (7)$$

$$V_{ERROR} = (SS_T - \Sigma_{F=A}^E SS_F)/(m(x-1)) = 40.65336873 \quad (8)$$

The relative contribution of factor F to the response is calculated using the following equation:

$$\rho_F = 100(SS_F - (DF_F)(V_{ER}))/SS_T \quad (9)$$

Values of $\rho_F$ for each factor are summarized Table 7:

TABLE 7

$\rho_F$ Values

| Factor | | $\rho_F$ |
|---|---|---|
| L | $\rho_A =$ | 25.2873 |
| H | $\rho_B =$ | 0.96724 |
| C | $\rho_C =$ | 3.95505 |
| S | $\rho_D =$ | 44.002 |
| A | $\rho_E =$ | 21.3081 |

The $M_i^F$ from Table 3 and the $SS_F$ values from Table 5 for the factors are summarized in the Table 8 below, together with the ranges of the $M_i^F$ for each factor. The relative contributions of each factor correspond to decreasing order of the $SS_F$'s and ranges.

TABLE 8

Significance Contributions of the Factors

| Levels | Factors | | | | |
|---|---|---|---|---|---|
| | L | H | C | S | A |
| 1 | 24.1663 | 28.684 | 28.1656 | 22.2047 | 31.9048 |
| 2 | 29.3194 | 29.2999 | 29.7369 | 28.0899 | 30.4899 |

TABLE 8-continued

Significance Contributions of the Factors

| | Factors | | | | |
|---|---|---|---|---|---|
| Levels | L | H | C | S | A |
| 3 | 33.1273 | 28.6581 | 28.7153 | 33.2146 | 27.3793 |
| 4 | 31.6323 | 31.6034 | 31.6275 | 34.7361 | 28.4713 |
| Range[a] | 8.96104 | 2.94531 | 3.46183 | 12.5314 | 4.52549 |
| $SS_F$ | 10906.3 | 534.461 | 1808.68 | 18887.6 | 9209.26 |
| Rank (Range)[b] | 2 | 5 | 4 | 1 | 3 |

[a]Range = $M_i^F$ (maximum) − $M_i^F$ (minimum)
[b]Significance Contribution: S > L > A > C > H Therefore, ANOVA calculations using the measured net current values in Table 2 identify scan rate, S, as the factor most contributing to the current response, followed in decreasing order by the variables L, A, C, and H.

Further examination of the $M_i^F$ values and their variations among the levels studied for each factor provide additional insight into the nature of the electrode and the chlorate electroreduction process. For example, Table 3 identifies a film having L/3=5 bilayers as the most efficient in promoting maximum current response. The thinner 3 and 4 bilayer films and the thicker 6 bilayer film provide lower responses, as indicated by their $M_i^L$ values. The proportional current reductions noted for the 3 and 4 bilayer films can be ascribed to the presence of less redox active $PMo_{11}V$ in these thinner films. In contrast, the 6 bilayer film contains the most $PMo_{11}V$ yet also exhibits decreased current compared to the 5 bilayer film. The 6 bilayer film corresponds approximately to the absorbance break point in FIG. 1B, at which differences in film packing ostensibly occur as oxidation of the blue $V^{IV}$ form of the $PMo_{11}V$ solution species deposited to the orange $V^V$ form is completed. Associated changes in packing density and internal film structure, together with increased separation between the underlying electrode and solution as film thickness increases, resulting in lowered film permeability and currents provide an explanation for the observations consistent with similar behavior noted for corresponding thick $(PR/PMo_{11}V)_n$ films (n≥5) elsewhere.[46]

Not surprisingly, film aging also significantly affects the current response. The largest $M_i^A$ in Table 3 is observed using the films aged 1 week. Thereafter, current response falls until the film has aged 5 weeks, then recovers slightly (~10%) for the 8 week old film. This behavior indicates some restructuring of the films as they age, leading to changes in permeability and mechanical properties reflected in the current response. Similar behaviors have been noted for paraquat-silicate[49,55,56] and polyelectrolyte multilayer[57-61] films, in which components are usually deposited in kinetically trapped conformations that slowly relax via chemical or physical processes, respectively, to their thermodynamically stable equilibrium conformations as the films age. That similar phenomena related to changes in internal structure occur in the films is also supported by observations of slight changes in film absorbance noted by Fernandes, et. al.[46] in analogous $(PR/PMo_{11}V)_n$ films following overnight drying/re-wetting cycles during film deposition.

The pH dependence in Table 3 indicates that current is generally enhanced by increasing the solution pH, although the changes in $M_i^H$ are non-monotonic suggesting that factor H may be strongly influenced by one or more other factors in the system. Nevertheless, the H/4=2.85 pH solution provides the largest response. This contrasts with behaviors noted for chlorate electroreduction by other polyoxometalates[21,62,63] for which reduction is generally more favorable at lower pH. Chlorate electroreduction can occur in both acidic and basic solutions,[6,40] with reduction in acidic solution thermodynamically much more favorable:

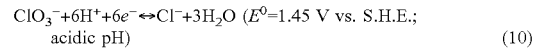
$ClO_3^- + 6H^+ + 6e^- \leftrightarrow Cl^- + 3H_2O$ ($E^0$=1.45 V vs. S.H.E.; acidic pH) (10)

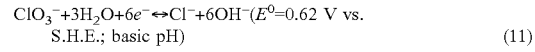
$ClO_3^- + 3H_2O + 6e^- \leftrightarrow Cl^- + 6OH^-$ ($E^0$=0.62 V vs. S.H.E.; basic pH) (11)

The fact that chlorate electroreduction for the films is somewhat more favorable at higher pH suggests that reduction may occur primarily via eq. (11), rather than eq. (10). Contributions to chlorate reduction via eq. (11) are supported by the structure of the films, which are terminated by a layer of cationic, hydrophobic PR species also contained within the film interior. The PR component is expected to provide an electrostatic and hydrophobic barrier inhibiting entry of protons, which possess a high charge density and highly structured water solvent shell, into the film. In contrast, for a neutral molecule such as water or poorly solvated chaotropic anions[64] such as $ClO_3^-$ or $Cl^-$, which possess zero or favorable (i.e., anionic) lower charge densities, respectively, entry required to complete the electroreduction is more facile.[65]

For the S and C factors changes in current response are generally consistent with expectations for CV measurements. For example, CV currents increase with scan rate, S, which reflects the change in driving force for the reaction at the electrode. $M_i^S$ values in Table 3 increase in a monotonic fashion with S as expected, with maximum current observed for the fastest scan rate, S/4. In similar manner, the largest current response occurs at the highest chlorate concentration (C/4=1000 µM), consistent with the current vs. [$ClO_3^-$] response already noted in FIG. 4B. The non-monotonic change in $M_i^C$ on proceeding from level i=1 to i=4, however, is analogous to that observed for pH with $M_i^H$, again suggesting that one or more other factors, such as film age, may interact with and alter the chlorate concentration effect. These non-monotonic variations in $M_i^C$ and $M_i^H$ are discussed further below.

Electrode Performance Model—

In conjunction with the Taguchi study, experiments were also conducted using a two-level full factorial design to obtain a mathematical model for the system. Given the age effect results noted for the films from the Taguchi analysis, study was directed to films aged 8 weeks that had reached their thermodynamic equilibrium. Therefore the design probed only the effects of the factors, L, H, C, and S, each examined at two levels using coded levels (i.e., ±1) for each factor as defined by eq. (12):

$$p = 2(q-a)/(b-a) - 1 \qquad (12)$$

In eq. (12), a and b represent the low and high values for a given factor associated with its −1 and +1 coded values in the design; q is any intermediate value for the factor within the range a≤q≤b; and p is its corresponding value linearly mapped onto the 1≤p≤+1 range. The values of L=−1≡3 bilayers and L=+1≡5 bilayers were chosen to further investigate the region of monotonic increase in current with increased bilayer number identified by the Taguchi design. For the solution pH factor, H was defined directly in terms of [H⁺] in solution, rather than the pH values associated with each solution, with H=−1≡0.0014 M HCl (i.e., pH 2.85) and H=+1≡0.0479 M HCl (i.e., pH 1.32). For the remaining factors, coded levels corresponded to the minimum and maximum values of each factor used in the Taguchi design as follows: C=−1≡250 μM ClO$_3^-$ and C=+1≡1000 μM ClO$_3^-$; and S=1≡50 mV·s$^{-1}$ and S=+1≡200 mV·s$^{-1}$.

A standard order design matrix of the $2^4$=16 possible combinations of factor levels was prepared as shown in Table 9, which also summarizes the net current measurements and provides the average current observed and its standard deviation for each experiment comprising the two-level full factorial design for the 8 week old film electrodes

TABLE 9

Standard Order Design Matrix and Measured Net Currents

| Expt. No.[a] | Factors | | | | Net Currents (μA) | | | | |
|---|---|---|---|---|---|---|---|---|---|
| | L | H | C | S | $i_1$ | $i_2$ | $i_3$ | $i_{ave}$ (μA)[c] | $\sigma_i$ (μA)[d] |
| 1 | −1[b] | −1 | −1 | −1 | 13.18 | 10.68 | 9.57 | 11.14 | 1.85 |
| 2 | +1 | −1 | −1 | −1 | 20.97 | 16.86 | 15.14 | 17.66 | 3.00 |
| 3 | −1 | +1 | −1 | −1 | 8.23 | 6.69 | 6.04 | 6.98 | 1.12 |
| 4 | +1 | +1 | −1 | −1 | 12.20 | 9.85 | 8.87 | 10.31 | 1.71 |
| 5 | −1 | −1 | +1 | −1 | 15.99 | 13.26 | 11.99 | 13.74 | 2.04 |
| 6 | +1 | −1 | +1 | −1 | 25.49 | 20.93 | 18.99 | 21.81 | 3.34 |
| 7 | −1 | +1 | +1 | −1 | 11.66 | 9.92 | 9.06 | 10.21 | 1.32 |
| 8 | +1 | +1 | +1 | −1 | 25.41 | 19.85 | 17.83 | 21.03 | 3.93 |
| 9 | −1 | −1 | −1 | +1 | 50.23 | 39.93 | 36.23 | 42.13 | 7.25 |
| 10 | +1 | −1 | −1 | +1 | 71.22 | 58.45 | 53.28 | 60.98 | 9.24 |
| 11 | −1 | +1 | −1 | +1 | 26.25 | 20.82 | 19.17 | 22.08 | 3.70 |
| 12 | +1 | +1 | −1 | +1 | 42.20 | 33.71 | 31.04 | 35.65 | 5.83 |
| 13 | −1 | −1 | +1 | +1 | 52.95 | 43.11 | 39.27 | 45.11 | 7.06 |
| 14 | +1 | −1 | +1 | +1 | 80.70 | 67.15 | 61.37 | 69.74 | 9.92 |
| 15 | −1 | +1 | +1 | +1 | 34.71 | 29.42 | 27.59 | 30.57 | 3.70 |
| 16 | +1 | +1 | +1 | +1 | 58.58 | 47.53 | 43.90 | 50.01 | 7.65 |

[a]Experiment number. Each row in the matrix specifies coded values per eq. (12) for each factor used in that experiment as specified in the Factors column.
[b]Coded ± 1 level for the factors.
[c]Average current calculated from net currents as $i_{ave} = (i_1 + i_2 + i_3)/3$
[d]Standard deviation.

Table 10 summarizes the calculation of the Effects from the average currents measured for each experiment using Yates' Algorithm.[52] Effects are identified with the appropriate factor or combination of factors. Identical values obtained for a "Squares Check" for each column of the Yates matrix confirms that the calculations are correct.

The probability of each Effect occurring solely due to random error was computed using eq. (13):

$$P_j = 100(j - \tfrac{1}{2})/15 \quad (j=1\text{-}15 \text{ Effects}) \tag{13}$$

In eq. (13), $P_j$ is the probability that the $j^{th}$ Effect is statistically non-significant and occurs simply due to random error. The Effects are ordered from most negative to most positive and assigned the appropriate $P_j$ value from eq. (13), as summarized in Table 11 below.

Figure 5:
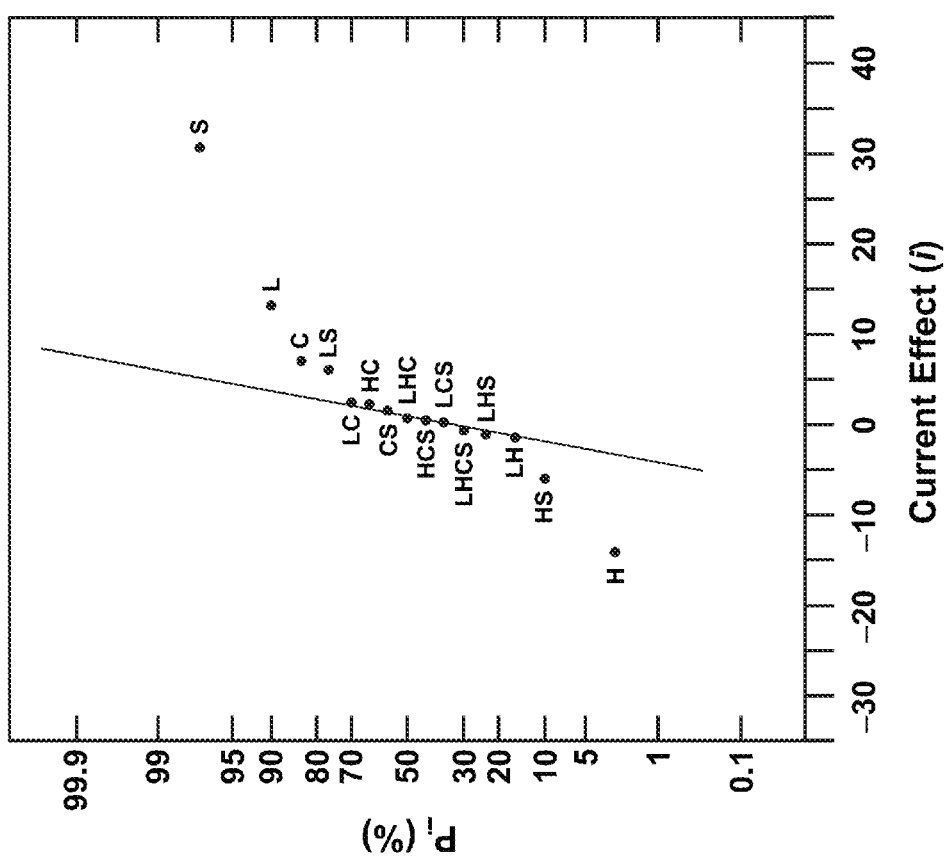
FIG. 5 is a normal probability plot of Effects, namely a plot of current Effects from Table 11 vs. probability of random occurrence, P. Effects comprising the straight line portion of the plot are ascribed to random error. The Effects deviating from the line make statistically significant contributions to the observed current. Letters identify the factor or factor interactions corresponding to each point.

The normal probability plot of the Effects vs. $P_j$ data from Table 11 is shown in FIG. 5. Nine points comprise the straight line section of the plot, signifying Effects that are statistically non-significant and can be attributed to random error. The remaining 6 points deviating from the straight line portion of the plot represent Effects that provide statistically significant contributions to the observed current response. These comprise the Effects due to the L, S, H, and C factors and the HS and LS factor interactions.

TABLE 11

Two-level Full Factorial Design Effects & Probabilities Due to Random Error

| Expt. No. | Factors (F)[a] | | | | Average Current, $i_{ave}$ (μA)[b] | Effect ID[c] | Effect (E)[d] | Probability ($P_j$)[e] | Order (j)[f] |
|---|---|---|---|---|---|---|---|---|---|
| | L | H | C | S | | | | | |
| 1 | −1 | −1 | −1 | −1 | 11.14 | Average | 29.32 | — | — |
| 2 | +1 | −1 | −1 | −1 | 17.66 | L | 13.15 | 90.000 | 14 |
| 3 | −1 | +1 | −1 | −1 | 6.98 | H | −11.93 | 3.333 | 1 |
| 4 | +1 | +1 | −1 | −1 | 10.31 | LH | −1.36 | 16.667 | 3 |
| 5 | −1 | −1 | +1 | −1 | 13.74 | C | 6.91 | 83.333 | 13 |
| 6 | +1 | −1 | +1 | −1 | 21.80 | LC | 2.58 | 70.000 | 11 |
| 7 | −1 | +1 | +1 | −1 | 10.21 | HC | 2.29 | 63.333 | 10 |
| 8 | +1 | +1 | +1 | −1 | 21.03 | LHC | 0.75 | 50.000 | 8 |
| 9 | −1 | −1 | −1 | +1 | 42.13 | S | 30.42 | 96.667 | 15 |
| 10 | +1 | −1 | −1 | +1 | 60.98 | LS | 5.97 | 76.667 | 12 |
| 11 | −1 | +1 | −1 | +1 | 22.08 | HS | −7.98 | 10.000 | 2 |
| 12 | +1 | +1 | −1 | +1 | 35.65 | LHS | −1.26 | 23.333 | 4 |

TABLE 10

Summary of Yates' Algorithm Calculation of Effects

| Expt. No. | $i_{ave}$ (μA) | Column Number, y[a] | | | | Divisor | Effect E[b] | Effect ID[c] |
|---|---|---|---|---|---|---|---|---|
| | | 1 | 2 | 3 | 4 | | | |
| 1 | 11.14393 | 28.80073 | 46.092 | 112.8869 | 469.1537 | 16 | 29.3221 | Average |
| 2 | 17.6568 | 17.29127 | 66.7949 | 356.2668 | 105.1995 | 8 | 13.14993 | L |
| 3 | 6.984133 | 35.5498 | 160.8378 | 28.7131 | −95.4592 | 8 | −11.9324 | H |
| 4 | 10.30713 | 31.2451 | 195.4289 | 76.48637 | −10.9119 | 8 | −1.363992 | LH |
| 5 | 13.7442 | 103.1071 | 9.835867 | −15.8142 | 55.294 | 8 | 6.91175 | C |
| 6 | 21.8056 | 57.7307 | 18.87723 | −79.645 | 20.67393 | 8 | 2.584242 | LC |
| 7 | 10.21463 | 114.8488 | 32.4269 | −0.43543 | 18.3126 | 8 | 2.28908 | HC |
| 8 | 21.03047 | 80.58017 | 44.05947 | −10.4765 | 6.032667 | 8 | 0.75408 | LHC |
| 9 | 42.12623 | 6.512867 | −11.5095 | 20.7029 | 243.3799 | 8 | 30.42248 | S |
| 10 | 60.9809 | 3.23 | −4.3047 | 34.5911 | 47.77327 | 8 | 5.971658 | LS |
| 11 | 22.07923 | 8.0614 | −45.3764 | 9.041367 | −63.8309 | 8 | −7.978858 | HS |
| 12 | 35.65147 | 10.81583 | −34.2686 | 11.63257 | −10.0411 | 8 | −1.255133 | LHS |
| 13 | 45.111 | 18.85467 | −3.18987 | 7.204767 | 13.8882 | 8 | 1.736025 | CS |
| 14 | 69.73777 | 13.57223 | 2.754433 | 11.10783 | 2.5912 | 8 | 0.3239 | LCS |
| 15 | 30.57373 | 24.62677 | −5.28243 | 5.9443 | 3.903067 | 8 | 0.48788 | HCS |
| 16 | 50.00643 | 19.4327 | −5.19407 | 0.088367 | −5.85593 | 8 | −0.731992 | LHCS |
| | 19387.54 | 38775.07 | 77550.14 | 155100.3 | 310200.6 | | =Sum of Squares = Q[d] | |
| | 19387.54 | 19387.54 | 19387.54 | 19387.54 | 19387.54 | | =Q/$2^y$ (Squares Check) | |

[a]Yates' Algorithm matrix elements.
[b]Effect calculated by dividing each element of Column 4 by the corresponding Divisor.
[c]Factor or factor interaction associated with each Effect.
[d]Sum of the squares of each entry in column y.

TABLE 11-continued

Two-level Full Factorial Design Effects & Probabilities Due to Random Error

| Expt. No. | Factors (F)[a] | | | | Average Current, $i_{ave}$ (μA)[b] | Effect ID[c] | Effect (E)[d] | Probability $(P_j)$[e] | Order (j)[f] |
|---|---|---|---|---|---|---|---|---|---|
| | L | H | C | S | | | | | |
| 13 | −1 | −1 | +1 | +1 | 45.11 | CS | 1.74 | 56.667 | 9 |
| 14 | +1 | −1 | +1 | +1 | 69.74 | LCS | 0.32 | 36.667 | 6 |
| 15 | −1 | +1 | +1 | +1 | 30.57 | HCS | 0.49 | 43.333 | 7 |
| 16 | +1 | +1 | +1 | +1 | 50.01 | LHCS | −0.73 | 30.000 | 5 |

[a]Coded factor levels defined in eq. (12).
[b]Average of 3 net current measurements from Table 9.
[c]Identification of factors and/or factor interactions associated with calculated Effects.
[d]Effects calculated using the Yates' Algorithm in Table 10.
[e]Probability of the Effect being due solely to random error calculated using eq. (13).
[f]Numerical order of the Effects from most negative to most positive for probability of random occurrence assignment, $P_j$, using eq. (13).

ANOVA calculations can be used to verify the significance of the S, L, H, C factors and HS and LS factor interactions identified in FIG. 5. Table 12 summarizes the calculations of the average net current ($i_{ave}$), degrees of freedom (DF) and variance (V) for each factorial experiment, "i". The terms are defined as follows for the "$i^{th}$" experiment:

$$(i_{ave})_i = (i_1 + i_2 + i_3)_i / x \text{ (where } x=3 \text{ replicate current measurements per experiment)} \quad (14)$$

$$DF_i = x - 1 = 3 - 1 = 2 \quad (15)$$

$$V_i = ((i_1 - i_{ave})^2 + (i_2 - i_{ave})^2 + (i_3 - i_{ave})^2)_i / DF_i \quad (16)$$

TABLE 12

Calculation of the Current Averages, Degrees of Freedom, and Variance

| Expt. No. (i) | Factors | | | | Net Current | | | | DF | V |
|---|---|---|---|---|---|---|---|---|---|---|
| | L | H | C | S | $i_1$(μA) | $i_2$(μA) | $i_3$(μA) | $i_{ave}$(μA) | | |
| 1 | −1 | −1 | −1 | −1 | 13.18 | 10.68 | 9.57 | 11.14333 | 2 | 3.41903 |
| 2 | +1 | −1 | −1 | −1 | 20.97 | 16.86 | 15.14 | 17.65667 | 2 | 8.97323 |
| 3 | −1 | +1 | −1 | −1 | 8.23 | 6.69 | 6.04 | 6.986667 | 2 | 1.26503 |
| 4 | +1 | +1 | −1 | −1 | 12.20 | 9.85 | 8.87 | 10.30667 | 2 | 2.92863 |
| 5 | −1 | −1 | +1 | −1 | 15.99 | 13.26 | 11.99 | 13.74667 | 2 | 4.17763 |
| 6 | +1 | −1 | +1 | −1 | 25.49 | 20.93 | 18.99 | 21.80333 | 2 | 11.1345 |
| 7 | −1 | +1 | +1 | −1 | 11.66 | 9.92 | 9.06 | 10.21333 | 2 | 1.75453 |
| 8 | +1 | +1 | +1 | −1 | 25.41 | 19.85 | 17.83 | 21.03 | 2 | 15.4084 |
| 9 | −1 | −1 | −1 | +1 | 50.23 | 39.93 | 36.23 | 42.13 | 2 | 52.63 |
| 10 | +1 | −1 | −1 | +1 | 71.22 | 58.45 | 53.28 | 60.98333 | 2 | 85.2742 |
| 11 | −1 | +1 | −1 | +1 | 26.25 | 20.82 | 19.17 | 22.08 | 2 | 13.7223 |
| 12 | +1 | +1 | −1 | +1 | 42.20 | 33.71 | 31.04 | 35.65 | 2 | 33.9591 |
| 13 | −1 | −1 | +1 | +1 | 52.95 | 43.11 | 39.27 | 45.11 | 2 | 49.7856 |
| 14 | +1 | −1 | +1 | +1 | 80.70 | 67.15 | 61.37 | 69.74 | 2 | 98.4433 |
| 15 | −1 | +1 | +1 | +1 | 34.71 | 29.42 | 27.59 | 30.57333 | 2 | 13.6712 |
| 16 | +1 | +1 | +1 | +1 | 58.58 | 47.53 | 43.90 | 50.00333 | 2 | 58.4636 |

From Table 12, the total number of current measurements for 16 experiments each replicated 3 times is N=48. The grand average response and the sum of the degrees of freedom are given by the following:

$$\text{Grand Average} = 29.32 = \Sigma_{i=1}^{16} (i_1 + i_2 + i_3)_i / N \quad (17)$$

$$DF_T = 32 = \Sigma_{i=1}^{16} (DF)_i \quad (18)$$

Therefore, the mean square error (MSE) for the system is given by:

$$MSE = 28.4382 = \Sigma_{i=1}^{16} (DF)_i \cdot (V)_i / DF_T \quad (19)$$

Table 13 summarizes the $(MSB)_i$ values calculated from each Effect, $E_i$.

TABLE 13

MSB Calculations

| Effect ID | Effect $E_i$ | $E_i^2$ | N | $(MSB)_i$ |
|---|---|---|---|---|
| L | 13.1499 | 172.921 | 48 | 2075.05 |
| H | −11.932 | 142.382 | 48 | 1708.59 |
| LH | −1.364 | 1.86047 | 48 | 22.3257 |
| C | 6.91175 | 47.7723 | 48 | 573.267 |
| LC | 2.58424 | 6.6783 | 48 | 80.1397 |
| HC | 2.28908 | 5.23986 | 48 | 62.8784 |
| LHC | 0.75408 | 0.56864 | 48 | 6.8237 |
| S | 30.4225 | 925.527 | 48 | 11106.3 |
| LS | 5.97166 | 35.6607 | 48 | 427.928 |
| HS | −7.9789 | 63.6622 | 48 | 763.946 |
| LHS | −1.2551 | 1.57536 | 48 | 18.9043 |
| CS | 1.73603 | 3.01378 | 48 | 36.1654 |
| LCS | 0.3239 | 0.10491 | 48 | 1.25893 |
| HCS | 0.48788 | 0.23803 | 48 | 2.85636 |
| LHCS | −0.732 | 0.53581 | 48 | 6.42974 |

There are $DF_{MSE}=32$ and $DF_{MSB}=1$ for this factorial design. In order to test the hypothesis ($H_1$) that a given Effect is statistically significant vs. the null hypothesis ($H_0$) that the Effect is not statistically significant, the $(MSB)_i$ is compared to the MSE by defining the $(F_0)_i$ ratio:

$$(F_0)_i = (MSB)_i / MSE \quad (21)$$

The $(F_0)_i$ are compared to the corresponding $F_c$ value, taken from an F-distribution table, that would be expected if a given $E_i$ is due to random error. For the systems, the appropriate $F_C$ is of the form $F_C(0.999, DF_{MSB}, DF_{MSE}) = F_C(0.999, 1, 32)$, where 0.999 represents the confidence limit for the significance evaluation. The F-distribution table does not include values for $DF_{MSE}=32$, so the more conservative available $F_C(0.999, 1, 30)=13.3$ is used instead. The ratio $(F_0)_i / F_C$ is formed for each effect, $E_i$. Values of $(F_0)_i / F_C > 1$ correspond to statistically significant $E_i$, at the 0.999 confidence level, whereas values less than one correspond to $E_i$ associated with random error. Table 14 summarizes these calculation.

TABLE 14

ANOVA Identification of Statistically Significant Effects

| (MSB)$_i$ | MSE | (F$_0$)$_i$ | F$_C$(0.999, 1, 30) | (F$_0$)$_i$/F$_C$ | Significance (F$_0$)$_i$/F$_C$ > 1 | Effect ID |
|---|---|---|---|---|---|---|
| 2075.05 | 28.4382 | 72.9671 | 13.3 | 5.48625 | Yes | *L* |
| 1708.59 | 28.4382 | 60.0808 | 13.3 | 4.51735 | Yes | *H* |
| 22.3257 | 28.4382 | 0.78506 | 13.3 | 0.05903 | No | LH |
| 573.267 | 28.4382 | 20.1584 | 13.3 | 1.51567 | Yes | *C* |
| 80.1397 | 28.4382 | 2.81803 | 13.3 | 0.21188 | No | LC |
| 62.8784 | 28.4382 | 2.21106 | 13.3 | 0.16624 | No | HC |
| 6.8237 | 28.4382 | 0.23995 | 13.3 | 0.01804 | No | LHC |
| 11106.3 | 28.4382 | 390.543 | 13.3 | 29.3642 | Yes | *S* |
| 427.928 | 28.4382 | 15.0477 | 13.3 | 1.13141 | Yes | *LS* |
| 763.946 | 28.4382 | 26.8634 | 13.3 | 2.01981 | Yes | *HS* |
| 18.9043 | 28.4382 | 0.66475 | 13.3 | 0.04998 | No | LHS |
| 36.1654 | 28.4382 | 1.27172 | 13.3 | 0.09562 | No | CS |
| 1.25893 | 28.4382 | 0.04427 | 13.3 | 0.00333 | No | LCS |
| 2.85636 | 28.4382 | 0.10044 | 13.3 | 0.00755 | No | HCS |
| 6.42974 | 28.4382 | 0.2261 | 13.3 | 0.017 | No | LHCS |

Statistically significant effects at the 0.999 confidence level are shown in bold italic typeface in Table 14. The L, H, C, S, HS, and LS Effects identified as statistically significant in Table 14 are identical to and confirm those identified graphically in FIG. 5.

The results of the two-level full factorial study are generally consistent with those of the Taguchi design. The largest Effects are those due to the S (i.e., 30.42) and L (i.e., 13.15) factors, which provide positive contributions to the observed current as their values increase within the range of values studied. The contribution of the H factor (i.e., −11.93) is negative,[66] with increasing acidity (i.e., lower pH) diminishing the current. These Effects are augmented by smaller (relative to the S and L Effects) antagonistic HS (i.e., −7.98) and synergistic LS (i.e., 5.97) interactions that further alter current response in the system.

The relative contribution of the H (i.e., −11.93) factor exceeds that of the C (i.e., 6.91) factor in Table 11, in opposition to the ANOVA results from the Taguchi design. However, the Taguchi design includes the film age factor, A, whereas film age was not examined in the two-level full factorial design. This behavior suggests that current contributions from factors C and/or H are affected by film age. Factor C appears independently of interactions with other factors in FIG. 5, suggesting that a CA interaction may be responsible at least in part for the non-monotonic behavior of the $M_i^C$ in the Taguchi design of Table 3. Such behavior is consistent with previous observations of contributions of anion-film age interactions on current responses in paraquat-silicate thin film electrodes.[55,56] Interpretation of the non-monotonic behavior of the $M_i^H$ in Table 3, however, is complicated by the combined effects of HA interactions, if any, and the HS interaction noted in FIG. 5, which is of significant magnitude relative to the H Effect (i.e., −7.98 vs. −11.93, respectively).

The results from FIG. 5 support a model of the general form shown in eq. (22) describing the current response of the 8 week old films in terms of the average system response and half the sum of the products of the significant Effects, E, and corresponding coded factors, F:

$$i = \text{Average} + \tfrac{1}{2}\Sigma_j(E_j)(F_j) \tag{22}$$

Using the appropriate values for the statistically significant Effects from Table 14 yields eq. (23) as a model for the 8 week old film electrodes in terms of the coded values of the statistically significant factors and factor interactions identified in FIG. 5:

$$i = 29.32 + \tfrac{1}{2}[30.42S + 13.15L - 11.93H - 7.98HS + 6.91C + 5.97LS] \tag{23}$$

For an electrode comprising a fixed number of bilayers (L) immersed in a solution of fixed acidity/pH (H) operating at a constant scan rate (S), eq. (23) correctly predicts a linear variation of current with chlorate concentration (C) consistent with the observations in FIG. 4B.

The suitability of eq. (23) as a model equation for the electrodes can be further tested by calculating the differences (i.e., residuals, $\Delta R_i$) between the currents measured in Table 11 and those calculated from eq. (23) using the coded values of each factor in each experiment. Table 15 summarizes the calculations of the residuals using the Reverse Yates' Algorithm.[52] Column 4 from Table 10 above is inverted and inserted into Table 15 as Modified Column 4 after setting entries to zero that correspond to the non-significant effects determined from FIG. 5 in the main text. The Reverse Yates' matrix calculations using the values shown in Modified Column 4 are summarized in the "Reverse Column" portion of Table 15. The calculated value of the current, $i_{calc}$, is obtained by dividing the value shown in Column 4 by a divisor of 16 for each of the experiments of the two-level factorial design. The difference between the $i_{calc}$ and the corresponding measured current, $i_{ave}$, for each experiment constitutes the residual value, $\Delta R_i$. Identical values obtained for a "Squares Check" for each column of the reverse Yates matrix confirms that the calculations are correct.

TABLE 15

Summary of Residuals Calculations Using the Reverse Yates' Algorithm

| Effect ID | Modified Col. 4 | Reverse Column, y | | | | $i_{calc}$ (µA) | $i_{ave}$ (µA) | $\Delta R_i$ (µA) |
|---|---|---|---|---|---|---|---|---|
| | | 1 | 2 | 3 | 4 | | | |
| LHCS | 0 | 0 | 0 | 227.3223 | 761.5102 | 47.59 | 50.01 | 2.42 |
| HCS | 0 | 0 | 227.3223 | 534.1879 | 455.5647 | 28.47 | 30.57 | 2.10 |
| LCS | 0 | −63.8309 | 55.294 | 131.7757 | 1080.09 | 67.50 | 69.74 | 2.24 |

TABLE 15-continued

Summary of Residuals Calculations Using the Reverse Yates' Algorithm

| Effect ID | Modified Col. 4 | Reverse Column, y | | | | $i_{calc}$ (μA) | $i_{ave}$ (μA) | $\Delta R_i$ (μA) |
|---|---|---|---|---|---|---|---|---|
| | | 1 | 2 | 3 | 4 | | | |
| CS | 0 | 291.1531 | 478.8939 | 323.789 | 774.1449 | 48.38 | 45.11 | −3.27 |
| LHS | 0 | 0 | 0 | 354.984 | 650.9222 | 40.68 | 35.65 | −5.03 |
| HS | −63.8309 | 55.294 | 131.7757 | 725.1063 | 344.9767 | 21.56 | 22.08 | 0.52 |
| LS | 47.77327 | −95.4592 | 55.294 | 259.4375 | 969.5023 | 60.59 | 60.98 | 0.39 |
| S | 243.3799 | 574.3531 | 268.495 | 514.7074 | 663.5569 | 41.47 | 42.13 | 0.66 |
| LHC | 0 | 0 | 0 | 227.3223 | 306.8657 | 19.18 | 21.03 | .85 |
| HC | 0 | 0 | 354.984 | 423.5999 | 192.0133 | 12.00 | 10.21 | −1.79 |
| LC | 0 | −63.8309 | 55.294 | 131.7757 | 370.1223 | 23.13 | 21.80 | −1.33 |
| C | 55.294 | 195.6066 | 669.8123 | 213.201 | 255.2699 | 15.95 | 13.74 | −2.21 |
| LH | 0 | 0 | 0 | 354.984 | 196.2777 | 12.27 | 10.31 | −1.96 |
| H | −95.4592 | 55.294 | 259.4375 | 614.5183 | 81.42527 | 5.09 | 6.98 | 1.89 |
| L | 105.1995 | −95.4592 | 55.294 | 259.4375 | 259.5343 | 16.22 | 17.66 | 1.44 |
| Ave. | 469.1537 | 363.9542 | 459.4134 | 404.1194 | 144.6819 | 9.04 | 11.14 | 2.10 |
| | 308932.4 | 617864.8 | 1235730 | 2471459 | 4942918 | =Sum of Squares = Q | | |
| | 308932.4 | 308932.4 | 308932.4 | 308932.4 | 308932.4 | =Q/$2^y$ (Squares Check) | | |

The 16 residuals, $\Delta R_i$, summarized in Table 15 are ordered from most negative to most positive and assigned probabilities of occurrence due to random error, $P_j$, using eq. (24):

$$P_j = 100(j-\tfrac{1}{2})/16 \ (j=1\text{-}16 \text{ Residuals}) \quad (24)$$

Table 16 summarizes the $\Delta R_i$, and associated $P_j$ for the j=16 residuals.

TABLE 16

Model Residuals

| Order | Residual ($\Delta R_i$) | Probability ($P_j$) |
|---|---|---|
| 1 | −5.03 | 3.125 |
| 2 | −3.27 | 9.375 |
| 3 | −2.21 | 15.625 |
| 4 | −1.96 | 21.875 |
| 5 | −1.79 | 28.125 |
| 6 | −1.33 | 34.375 |
| 7 | 0.39 | 40.625 |
| 8 | 0.52 | 46.875 |
| 9 | 0.65 | 53.125 |
| 10 | 1.44 | 59.375 |
| 11 | 1.85 | 65.625 |
| 12 | 1.90 | 71.875 |
| 13 | 2.10 | 78.125 |
| 14 | 2.10 | 84.375 |
| 15 | 2.23 | 90.625 |
| 16 | 2.41 | 96.875 |

Figure 6:
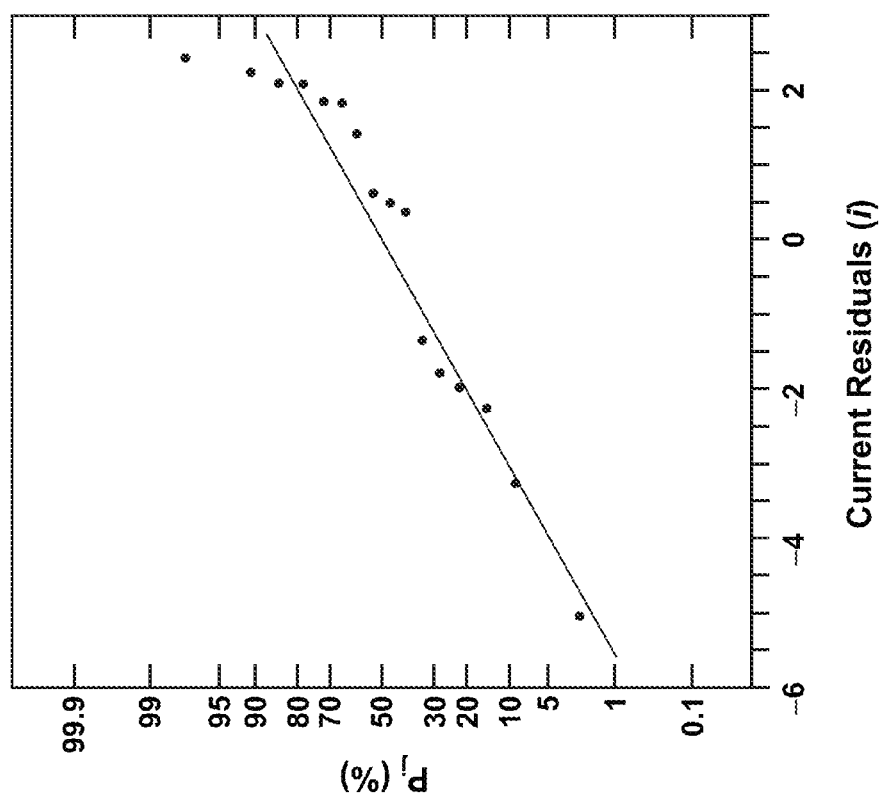
FIG. 6 is a normal probability plot of current residuals, namely a plot of current residuals ($\Delta R_i$) from Table 16 vs. probability of random occurrence, $P_j$.

The corresponding normal probability plot of the $\Delta R_i$ vs. $P_j$ from Table 16 is shown in FIG. 6 below. The plot is reasonably linear, with a range of $\Delta R_i$ (i.e., −5.03 μA≤$\Delta R_i$≤2.41 μA) approximately 10% that of the measured net currents (i.e., 6.98 μA≤$i_{ave}$≤69.74 μA) from Table 11. Consequently, eq. (23) provides a reasonable first approximation for the dependence of the current response on the statistically significant Effects and factors identified by the two-level factorial design.

Applications

The electrode comprises alternating layers vanadium-substituted phosphomolybdate polyoxometalate species and the dye, para-rosaniline. Either the para-rosaniline or the vanadium-substituted phosphomolybdate can be the outermost layer. Optionally, the electrode is formed on a substrate such as ITO, gold, platinum, glassy carbon, graphene, screen printed carbon, and/or another suitable substrate. The electrode is preferably porous. Embodiments have at least a total of four layers (two bilayers of vanadium-substituted phosphomolybdate polyoxometalate and para-rosaniline), optionally as many as 40 total layers (20 bilayers).

In use, the electrode can be contacted directly with soil and voltammetry performed. Preferably, the measurement is performed under damp, conductive conditions. In embodiments, the electrode and/or soil are first wetted with a solvent, for example by spraying one or both, and/or by dipping the electrode in solvent. In certain embodiments, electrical conductivity is assured by using an electrically conductive solvent, for example by including at least one salt in the solvent to form an electrolyte. Certain embodiments have the electrode contact soil through an intermediate paper (such as filter paper or chemwipe material) that has been wetted with a solvent, optionally an electrolyte. In other embodiments, the contact is direct with the soil in intimate contact with the electrode.

The electrode functions without the need to exclude or remove ambient oxygen. Furthermore the analysis can be done without a need to add strong acid (such as $HNO_3$, HCl, or $H_2SO_4$) and optionally can be done completely without pH adjustment, nor to acidify the soil or testing environment.

The solvent can be water and/or another solvent. In embodiments, the solvent comprises a deep eutectic solvent, for example a deep eutectic mixture of ethylene glycol and choline chloride such as can be obtained from a 2:1 mol ratio of ethylene glycol and choline chloride. Other suitable solvents include room temperature ionic liquids (RTILs, which are salts that are liquid at room temperature, not to be confused with salts dissolved in another liquid), and high-boiling (thus having a low evaporation rate) polar aprotic or protic solvents such as dimethyl sulfoxide (DMS) or dimethylformamide (DMF). A low rate of evaporation is desirable as it allows time for the analysis to be performed without requiring a sealed chamber or the like to reduce evaporation. Preferably, the solvent(s) are able to dissolve and extract chlorate from soils across a broad temperature range without significant evaporation. In embodiments, the solvent includes at least one salt (not necessarily an RTIL) in order to ensure conductivity.

Embodiments can include conventional computer hardware (e.g. a microprocessor, memory, etc.) and software sufficient to analyze the results of voltammetry performed by a potentiostat and to determine a likelihood of the presence or absence of chlorate in a sample and/or the expected concentration of chlorate in the sample (for example, by comparing the shape of a voltage/current curve received from a potentiostat to stored examples representing curves obtained from known chlorate concentrations), and optionally to transmit those results. Further embodiments can entail wireless transmission of potentiostat data to a separate device (for example a mobile device such as a cellphone or tablet) which is equipped with software and hardware sufficient to analyze the data and provide a reading of chlorate level. Such embodiments might reduce the circuit complexity, power requirement, and weight of the remote system.

A system for conducting the technique can include a potentiostat operably connected to an electrode comprising layers of vanadium-substituted phosphomolybdate alternating with layers of para-rosaniline, and computer hardware and software in communication with the potentiostat and configured to produce an output indicating a chlorate level in soil in contact with the electrode. Optionally, the system includes a reservoir of solvent and a valve configured to allow the solvent to wet the soil, electrode, and/or paper, thereby facilitating analysis.

In further embodiments, the electrode and potentiostat are carried by an unmanned vehicle such as an unmanned aerial vehicle, optionally with a radio transmitter configured to transmit the results of the analysis, or in the alternative configured to transmit potentiostat data as described above.

CONCLUDING REMARKS

A multilayer film, prepared via layer-by-layer deposition of cationic para-rosaniline acetate dye (i.e., PR) and the vanadium-containing Keggin-type $[PMo_{11}VO_{40}]^{5-}$ (i.e., $PVMo_{11}$) polyoxometalate anion, on indium tin oxide (ITO) provides an electrode for detection of chlorate. Taguchi L16 array and two-level full factorial statistically designed experiments were used to probe the current response as a function of the composition of the electrode and analyte solution. Performance was investigated as functions of the number of $PVMo_{11}$/PR electrode bilayers (L; 3-6 bilayers), solution acidity/pH (H; pH ~1.32-2.85), solution $[ClO_3^-]$ (C; 250-1000 μM), voltage scan rate (S; 50-200 mV·s$^{-1}$), and film age (A; 1-8 weeks).

The Taguchi L16 array results indicated that maximum current response was obtained using 1 week old electrodes comprising 5 $PVMo_{11}$/PR bilayers scanned at 200 mV·s$^{-1}$ in pH 2.85 solutions containing 1000 μM $ClO_3^-$. However, a significant film aging effect was also observed, consistent with relaxation of film components kinetically trapped during initial deposition to their equilibrium thermodynamic conformations with time, a process requiring at least 5 weeks at room temperature. A subsequent two-level full factorial design investigation of the effects due to the L, H, C, and S variables using 8 week old films identified the L, S, H, and C factors and HS and LS factor interactions as making statistically significant contributions to the observed current. A model describing the dependence of electrode current on the levels of these parameters was derived, which included and confirmed the linear dependence on $[ClO_3^-]$ noted in early experiments.

A key finding of this work was the insensitivity of the film/electrode to oxygen and common explosives such as TNT, which typically exhibit electrochemical signatures in the same region as the chlorate reduction and the polyoxometalate component of the films. In fact, linear dependence of current on chlorate concentration over a 0 μM≤ $[ClO_3^-]$≥1000 μM range in aerated 0.10 M sodium acetate pH 2.5 (aq) solution was demonstrated with a detection limit of ~220 μM $ClO_3^-$ (S/N>3). The ability to determine chlorate under ambient conditions in this manner and the insensitivity of the electrode to the presence of common N-based explosives bodes well for its eventual use in the field as a new tool to assist forces in the identification of IED manufacturing sites utilizing chlorate-based explosives. Work is currently in progress to understand and quantitatively map the effects of other environmental factors, such as temperature and humidity, on electrode preparation, storage, and performance and integrate the electrode system for deployment on unmanned aerial vehicle (UAV) platforms.

The major advantages of the described electrode are: (1) it is portable, small, and lightweight (as is the potentiostat/electronics needed to operate it); (2) the electrode operates without interference by oxygen, so it can be used in the field (unlike other chlorate sensing electrode systems, which required degassed solutions to function); (3) the electrode does not respond to the common explosives TNT and RDX, which would be expected to also occur in the environment for which use of the electrode is intended; (4) the electrode is rugged in that the composite film of para-rosaniline and vanadium-substituted phosphomolybdate adheres well to the indium tin oxide or glassy carbon electrode base substrate support; (5) the described electrode is easy to prepare via a simple dipcoating procedure that produces uniform and reproducible films of active para-rosaniline/vanadium-substituted phosphomolybdate composite; (6) the described para-rosaniline/vanadium-substituted phosphomolybdate composite film is stable in that it retains its activity for catalyzed electroreduction of chlorate even after 8 weeks of dry storage at room temperature.

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES AND END NOTES (1) Almaviva, S.; Chirico, R.; Nuvoli, M.; Palucci, A.; Schnurer, F.; Schweikert, W. *Talanta* 2015, 144, 420.
(2) Guo, Y. H.; Wang, X. T.; Miao, B.; Li, Y.; Yao, W. R.; Xie, Y. F.; Li, J. D.; Wu, D. M.; Pei, R. J. *Rsc Advances* 2015, 5, 98724.
(3) Jamil, A. K. M.; Izake, E. L.; Sivanesan, A.; Agoston, R.; Ayoko, G. A. *Analytical Methods* 2015, 7, 3863.
(4) Komarova, N. V.; Andrianova, M. S.; Gubanova, O. V.; Kuznetsov, E. V.; Kuznetsov, A. E. *Sensors and Actuators B-Chemical* 2015, 221, 1017.
(5) Giordano, B. C.; Field, C. R.; Andrews, B.; Lubrano, A.; Woytowitz, M.; Rogers, D.; Collins, G. E. *Analytical Chemistry* 2016, 88, 3747.
(6) Chiswell, B.; Keller-Lehmann, B. *Analyst* 1993, 118, 1457.
(7) Deshwal, B. R.; Lee, H.-K. *J Hazard Mater* 2004, 108, 173.

(8) Deshwal, B. R.; Lee, H. K. *J. Ind. Eng. Chem.* 2005, 11, 330.
(9) Pisarenko, A. N.; Stanford, B. D.; Quinones, O.; Pacey, G. E.; Gordon, G.; Snyder, S. A. *Anal. Chim. Acta* 2010, 659, 216.
(10) Garcia-Villanova, R. J.; Funcia, C. R.; Leite, M.; Fonseca, I. M. T.; Espinosa, M.; India, J. E. *J. Water Health* 2014, 12, 443.
(11) Burns, E. A. *Analytical Chemistry* 1960, 32, 1800.
(12) Urone, P.; Bonde, E. *Analytical Chemistry* 1960, 32, 1666.
(13) Trautwein, N. L.; Guyon, J. C. *Anal. Chim. Acta* 1968, 41, 275.
(14) Hosseini, S. G.; Pourmortazavi, S. M.; Gholivand, K. *Desalination* 2009, 245, 298.
(15) Oliveira, A. P.; Faria, R. B. *Journal of the American Chemical Society* 2005, 127, 18022.
(16) Galajda, M.; Lente, G.; Fábián, I. *Journal of the American Chemical Society* 2007, 129, 7738.
(17) Sant'Anna, R. T. P.; Monteiro, E. V.; Pereira, J. R. T.; Faria, R. B. *PLoS One* 2013, 8, Article No. e83706.
(18) Sant'Anna, R. T. P.; Faria, R. B. *PLoS One* 2014, 9, Article No. e109899.
(19) Rowe, A. A.; Bonham, A. J.; White, R. J.; Zimmer, M. P.; Yadgar, R. J.; Hobza, T. M.; Honea, J. W.; Ben-Yaacov, I.; Plaxco, K. W. *PLoS One* 2011, 6, Article No. e23783.
(20) Buldini, P. L.; Ferri, D.; Zignani, F. *Fresenius Z. Anal. Chem.* 1983, 314, 660.
(21) Pelzer, J.; Scholz, F.; Henrion, G.; Heininger, P. *Fresenius Z. Anal. Chem.* 1989, 334, 331.
(22) Yokoi, K.; van den Berg, C. M. G. *Anal. Chim. Acta* 1991, 245, 167.
(23) Gawryś, M.; Golimowski, J. *Anal. Chim. Acta* 2001, 427, 55.
(24) Krulic, D.; Larabi, N.; Fatouros, N. *Journal of Electroanalytical Chemistry* 2005, 579, 243.
(25) Safavi, A.; Shams, E. *Anlaytica Chimica Acta* 1999, 396, 215.
(26) Gao, Z.; Li, P.; Zhao, Z. *Talanta* 1991, 38, 1177.
(27) Gao, Z.; Wang, G.; Li, P.; Zhao, Z. *Analytical Chemistry* 1991, 63, 953.
(28) Gao, Z.; Ivaska, A.; Li, P. *Anal. Sci.* 1992, 8, 337.
(29) Gao, Z.; Siow, K. S. *Talanta* 1996, 43, 719.
(30) Gao, Z.; Siow, K. S.; Ng, A. *Electroanalysis* 1996, 8, 1183.
(31) Unoura, K.; Iwashita, A.; Itabashi, E.; Tanaka, N. *Bull. Chem. Soc. Jpn.* 1984, 57, 597.
(32) Ikeda, M.; Shimizu, K.; Sato, G. P. *Bull. Chem. Soc. Jpn.* 1982, 55, 797.
(33) Detusheva, L. G.; Kuznetsova, L. I.; Likholobov, V. A. *Russ Chem B+* 1993, 42, 1294.
(34) Tue-Ngeun, O.; Jakmunee, J.; Grudpan, K. *Talanta* 2005, 68, 459.
(35) Somnam, S.; Grudpan, K.; Jakmunee, J. *Mj. Int. J. Sci. Technol.* 2008, 2, 383.
(36) Xian, X. J.; Wen, S. M.; Deng, J. S.; Liu, J.; Nie, Q. *Can. Metall. Q.* 2012, 51, 133.
(37) Uçar, G. *Hydrometallurgy* 2009, 95, 39.
(38) Olanipekun, E. O.; Oderinde, R. A. *Trans. Indian Inst. Met.* 1999, 52, 391.
(39) Sattar, S.; Kustin, K. *Inorganic Chemistry* 1991, 30, 1668.
(40) Castellani, C. Bisi *Ann. Chim. (Rome)* 1959, 49, 2057.
(41) Meites, L.; Hofsass, H. *Analytical Chemistry* 1959, 31, 119.
(42) Ohura, H.; Imato, T.; Yamasaki, S. *Talanta* 1999, 49, 1003.
(43) Nylén, L.; Gustaysson, J.; Cornell, A. *Journal of the Electrochemical Society* 2008, 155, E136.
(44) Gustavsson, J.; Nylén, L.; Cornell, A. *J Appl. Electrochem.* 2010, 40, 1529.
(45) Cao, G.; Xiong, J.; Xue, Q.; Min, S.; Hu, H.; Xue, G. *Electrochim. Acta* 2013, 106, 465.
(46) Fernandes, D. M.; Teixeira, A.; Freire, C. *Langmuir* 2015, 31, 1855.
(47) Himeno, S.; Ishio, N. *Journal of Electroanalytical Chemistry* 1998, 451, 203.
(48) Chen, M. S.; Brandow, S. L.; Dulcey, C. S.; Dressick, W. J.; Taylor, G. N.; Bohland, J. F.; Georger, J. H.; Pavelchek, E. K.; Calvert, J. M. *J. Electrochem. Soc.* 1999, 146, 1421.
(49) Trammell, S. A.; Dressick, W. J.; Melde, B. J.; Moore, M. *J Phys. Chem. C.* 2011, 115, 13446.
(50) Golden, J.; Shriver-Lake, L.; Sapsford, K.; Ligler, F. *Methods* 2005, 37, 65.
(51) Zolfaghari, G.; Esmaili-Sari, A.; Anbia, M.; Younesi, H.; Amirmahmoodi, S.; Ghafari-Nazari, A. *J Hazard Mater* 2011, 192, 1046.
(52) Box, G. E. P.; Hunter, W S.; Hunter, J. S. *Statistics for Experimenters: An Introduction to Design, Data Analysis, and Model Building*; John Wiley & Sons, Inc.: New York, N.Y., 1978.
(53) Bonenfant, D.; Mimeault, M.; Hausler, R. *Industrial & Engineering Chemistry Research* 2003, 42, 3179.
(54) Fernandes, D. M.; Freire, C. *J. Appl. Electrochem.* 2014, 44, 655.
(55) Lebedev, N.; Trammell, S. A.; Dressick, W.; Kedziora, G. S.; Griva, I.; Schnur, J. M. *Photochemistry and Photobiology* 2011, 87, 1024.
(56) Trammell, S. A.; Tsoi, S.; Martin, B.; Melde, B. J.; Moore, M. M.; Dressick, W. J. *Journal of the Chemical Society—Chemical Communications* 2011, 47, 11348.
(57) Lulevich, V. V.; Nordschild, S.; Vinogradova, O. I. *Macromolecules* 2004, 37, 7736.
(58) Richert, L.; Engler, A. J.; Discher, D. E.; Picart, C. *Biomacromolecules* 2004, 5, 1908.
(59) Vinogradova, O. I. *J. Phys.-Condens. Matter* 2004, 16, R1105.
(60) Secrist, K. E.; Nolte, A. J. *Macromolecules* 2011, 44, 2859.
(61) Ge, A.; Matsusaki, M.; Qiao, L.; Akashi, M.; Ye, S. *Langmuir* 2016, 32, 3803.
(62) Dong, S.; Jin, W. *Journal of Electroanalytical Chemistry* 1993, 354, 87.
(63) Xue, G.; Xiong, J.; Guo, H.; Cao, G.; Nie, S.; Hu, H. *Electrochim. Acta* 2012, 69, 315.
(64) Jenkins, H. D. B.; Marcus, Y. *Chemical Reviews* 1995, 95, 2695.
(65) Hydrochloric acid (HCl) and chloric acid ($HClO_3$) are strong acids ($pK_a <$
(66) The negative contribution in this case is expected because the H factor in the Taguchi design is defined in terms of low vs. high pH.

What is claimed is:
1. A method of detecting chlorate in soil, the method comprising:
contacting soil wetted with a solvent containing an electrically conductive salt with an electrode comprising layers of vanadium-substituted phosphomolybdate alternating with layers of para-rosaniline, and
performing voltammetry with the electrode, wherein a catalytic reduction current indicates a likelihood of the presence or absence of chlorate in the soil.

2. The method of claim 1, wherein said vanadium-substituted phosphomolybdate is $Na_4H[(VMo_{11})O_{40}]$.

3. The method of claim 1, wherein the electrode comprises between 2 and 20 bilayers.

4. The method of claim 1, wherein said electrode further includes a substrate of indium tin oxide (ITO), gold, carbon, graphene, and/or screen printed carbon.

5. The method of claim 1, further comprising wetting the electrode with said solvent.

6. The method of claim 5, wherein said wetting is accomplished by using a paper wetted with said solvent between said soil and said electrode.

7. A method of detecting chlorate in soil, the method comprising:
contacting soil wetted with a solvent containing an electrically conductive salt with an electrode comprising layers of vanadium-substituted phosphomolybdate alternating with layers of para-rosaniline, and
performing voltammetry with the electrode, wherein a catalytic reduction current indicates a likelihood of the presence or absence of chlorate in the soil,
wherein the method is done without excluding or removing oxygen from the testing environment and furthermore without the use of strong acid.

8. The method of claim 7, wherein said vanadium-substituted phosphomolybdate is $Na_4H[(VMo_{11})O_{40}]$.

9. The method of claim 7, wherein the electrode comprises between 2 and 20 bilayers.

10. The method of claim 7, wherein said electrode further includes a substrate of indium tin oxide (ITO), gold, carbon, graphene, and/or screen printed carbon.

11. The method of claim 7, wherein said wetting is accomplished by using a paper wetted with said solvent between said soil and said electrode.

12. The method of claim 7, further comprising wetting the electrode with said solvent.

* * * * *